US012589231B2

(12) United States Patent
Tal

(10) Patent No.: US 12,589,231 B2
(45) Date of Patent: Mar. 31, 2026

(54) SUBCUTANEOUSLY CHANGEABLE VASCULAR ACCESS PORT

(71) Applicant: Portal Access, Inc., Wilmington, DE (US)

(72) Inventor: Michael Gabriel Tal, Tel Aviv (IL)

(73) Assignee: Portal Access Inc., Wilmington, DE (US)

(*) Notice: Subject to any disclaimer, the term of this patent is extended or adjusted under 35 U.S.C. 154(b) by 1016 days.

(21) Appl. No.: 17/435,475

(22) PCT Filed: Mar. 3, 2020

(86) PCT No.: PCT/US2020/020759
§ 371 (c)(1),
(2) Date: Sep. 1, 2021

(87) PCT Pub. No.: WO2020/180854
PCT Pub. Date: Sep. 10, 2020

(65) Prior Publication Data

US 2022/0134075 A1 May 5, 2022

Related U.S. Application Data

(60) Provisional application No. 62/961,374, filed on Jan. 15, 2020, provisional application No. 62/813,073, filed on Mar. 3, 2019.

(51) Int. Cl.
*A61M 39/02* (2006.01)

(52) U.S. Cl.
CPC . *A61M 39/0208* (2013.01); *A61M 2039/0223* (2013.01); *A61M 2039/0232* (2013.01); *A61M 2205/0216* (2013.01)

(58) Field of Classification Search
CPC ...... A61M 39/0208; A61M 2039/0223; A61M 2039/0232; A61M 2205/0216;
(Continued)

(56) References Cited

U.S. PATENT DOCUMENTS

| | | | |
|---|---|---|---|
| 4,886,501 | A | 12/1989 | Johnston et al. |
| 5,108,377 | A | 4/1992 | Cone et al. |

(Continued)

FOREIGN PATENT DOCUMENTS

| | | | |
|---|---|---|---|
| CA | 1151489 | A | 8/1983 |
| CN | 102421395 | A | 4/2012 |

(Continued)

OTHER PUBLICATIONS

U.S. Appl. No. 62/915,973, filed Oct. 16, 2019, Michael Gabriel Tal.

(Continued)

*Primary Examiner* — Theodore J Stigell
(74) *Attorney, Agent, or Firm* — Veros Legal Solutions, LLP

(57) ABSTRACT

Disclosed is a vascular access port selectively changeable subcutaneously from delivery configuration to deployed configuration. The vascular access port includes a port body and a port body extension being partly or wholly disengaged in the delivery configuration, and fixedly connected to form a unified structure of the vascular access port, greater in volume than the port body, in the deployed configuration. Methods and kits for deploying the vascular access port in a body of a subject are also disclosed.

20 Claims, 20 Drawing Sheets

(58) Field of Classification Search
CPC .. A61M 2039/0229; A61M 2039/0291; A61M 39/02
See application file for complete search history.

(56) References Cited

U.S. PATENT DOCUMENTS

| | | | |
|---|---|---|---|
| 5,246,424 | A | 9/1993 | Wilk |
| 5,387,192 | A | 2/1995 | Glantz et al. |
| 5,688,247 | A | 11/1997 | Haindl et al. |
| 5,716,326 | A | 2/1998 | Dannan |
| 6,033,390 | A | 3/2000 | von Dyck |
| 6,206,871 | B1 | 3/2001 | Zanon et al. |
| 6,213,973 | B1 | 4/2001 | Eliasen et al. |
| 6,258,058 | B1 | 7/2001 | Sanfilippo |
| 7,445,614 | B2 | 11/2008 | Bunodiere et al. |
| 7,708,722 | B2 | 5/2010 | Glenn |
| 8,025,639 | B2 | 9/2011 | Powers et al. |
| 8,282,610 | B1 | 10/2012 | Glenn |
| 8,317,761 | B2 | 11/2012 | Birk et al. |
| 8,545,460 | B2 | 10/2013 | Beasley et al. |
| 8,608,713 | B2 | 12/2013 | Beasley et al. |
| 8,876,788 | B2 * | 11/2014 | Glenn ............... A61M 39/0208 604/104 |
| 9,381,036 | B2 | 7/2016 | Rome et al. |
| 10,130,503 | B2 | 11/2018 | Couch et al. |
| 10,155,101 | B2 | 12/2018 | Wiley et al. |
| 2002/0010442 | A1 | 1/2002 | Teitelbaum |
| 2003/0018291 | A1 | 1/2003 | Hill et al. |
| 2004/0133173 | A1 | 7/2004 | Edoga et al. |
| 2004/0193119 | A1 | 9/2004 | Canaud et al. |
| 2004/0254537 | A1 | 12/2004 | Conlon et al. |
| 2005/0137537 | A1 | 6/2005 | Watson et al. |
| 2006/0217673 | A1 | 9/2006 | Schulze et al. |
| 2007/0010790 | A1 | 1/2007 | Byrum et al. |
| 2007/0123831 | A1 | 5/2007 | Haindl et al. |
| 2007/0161958 | A1 | 7/2007 | Glenn |
| 2008/0051722 | A1 | 2/2008 | Ellsmere et al. |
| 2008/0249509 | A1 | 10/2008 | Glenn |
| 2009/0030373 | A1 | 1/2009 | Gill |
| 2009/0093765 | A1 | 4/2009 | Glenn |
| 2009/0221976 | A1 | 9/2009 | Linden et al. |
| 2009/0259187 | A1 | 10/2009 | Egle et al. |
| 2009/0306606 | A1 | 12/2009 | Lancette et al. |
| 2010/0094335 | A1 | 4/2010 | Gerberding et al. |
| 2010/0262183 | A1 | 10/2010 | Abbott et al. |
| 2010/0286484 | A1 | 11/2010 | Stellon et al. |
| 2011/0034886 | A1 | 2/2011 | Elbe et al. |
| 2011/0213199 | A1 | 9/2011 | Franklin et al. |
| 2011/0245595 | A1 | 10/2011 | Birk et al. |
| 2011/0251453 | A1 | 10/2011 | Honaryar et al. |
| 2012/0059321 | A1 | 3/2012 | Hammond et al. |
| 2012/0065460 | A1 | 3/2012 | Nitka et al. |
| 2012/0245536 | A1 | 9/2012 | Gerber et al. |
| 2013/0012890 | A1 | 1/2013 | Glenn |
| 2013/0053783 | A1 | 2/2013 | Szweda et al. |
| 2013/0253263 | A1 | 9/2013 | Nitka et al. |
| 2014/0276900 | A1 | 9/2014 | Cote et al. |
| 2016/0106966 | A1 | 4/2016 | Jochum et al. |
| 2016/0213909 | A1 | 7/2016 | Davey et al. |
| 2016/0374655 | A1 | 12/2016 | Walters et al. |
| 2017/0072169 | A1 | 3/2017 | Jochum et al. |
| 2017/0165464 | A1 | 6/2017 | Jochum |
| 2018/0214680 | A1 | 8/2018 | Jho et al. |
| 2018/0264246 | A1 | 9/2018 | Lim et al. |
| 2020/0028847 | A1 | 1/2020 | Mizuno |
| 2022/0008706 | A1 | 1/2022 | Tal |
| 2022/0313972 | A1 | 10/2022 | Tal |
| 2023/0381479 | A1 | 11/2023 | Tal et al. |

FOREIGN PATENT DOCUMENTS

| | | | |
|---|---|---|---|
| CN | 102481201 | A | 5/2012 |
| CN | 105307716 | A | 2/2016 |
| CN | 114375214 | A | 4/2022 |
| CN | 116963797 | A | 10/2023 |
| EP | 2044889 | A1 | 4/2009 |
| GB | 2011173820 | | 11/2011 |
| GB | 2489518 | A | 10/2012 |
| JP | H3168159 | A | 7/1991 |
| JP | 2009536040 | A | 10/2009 |
| JP | 2013510652 | A | 3/2013 |
| WO | 2011094712 | A1 | 8/2011 |
| WO | 2013146307 | A1 | 10/2013 |
| WO | 2016004217 | A1 | 1/2016 |
| WO | 2019055037 | A1 | 3/2019 |
| WO | 2020028847 | A1 | 2/2020 |
| WO | 2020180854 | A1 | 9/2020 |
| WO | 2022011020 | A1 | 1/2022 |
| WO | 2022125661 | A1 | 6/2022 |

OTHER PUBLICATIONS

International Search Report and Written Opinion mailed Sep. 17, 2020 in International Patent Application No. PCT/US2020/041140.
International Search Report and Written Opinion mailed Oct. 22, 2021 in PCT/US2021/040699.
Communication pursuant to Article 94(3) EPC mailed on Jun. 16, 2025 in EP 20767305.4.
International Search Report, mailed Jun. 10, 2020.
ISA Written Opinion, mailing date Jun. 10, 2020.

* cited by examiner

SUBCUTANEOUSLY CHANGEABLE VASCULAR ACCESS PORT

RELATED APPLICATIONS

This application claims the benefit under 35 U.S.C. § 119(e) of U.S. Provisional Patent Application No. 62/813,073, filed on Mar. 3, 2019, titled SUBCUTANEOUSLY FORMABLE VASCULAR ACCESS PORT, and of U.S. Provisional Patent Application No. 62/961,374, filed on Jan. 15, 2020, titled SUBCUTANEOUSLY CHANGEABLE VASCULAR ACCESS PORT; the entire contents of which are hereby incorporated by reference herein.

BACKGROUND

The present disclosure, in some embodiments thereof, relates to devices and methods for facilitating and/or improving repeated deliveries of fluids (e.g., fluids carrying nutrients, medicament and/or agents such as chemotherapy agents) into vasculature of a subject, and more particularly, but not exclusively, to vascular access ports and methods of delivery and deployment thereof in a body of a subject.

Repeated needle pricking for facilitating delivery or withdrawal of fluids (e.g., medication or agents) to patient's vascular system causes harm to local tissues and decreases target blood vessel functionality and needle placement accuracy. This phenomenon is often evident in chronic diabetes, dialysis or chemotherapy patients, for example, who require continuous and repeated intravenous fluids administration for prolonged periods.

A vascular access port is a device that enables such repeated pricking and fluid administration while minimizing the accumulated harm caused by needle pricking and powered injections of fluid. The access port is subcutaneously implanted, in a surgically formed pocket in proximity to a large blood vessel, usually in the chest. It is basically formed of a port body enclosing a cavity, which is capped with a septum member configured for supporting the upper skin layers and for accepting repeated needle pricking therethrough for intravascular fluid deliveries sealed to the surrounding body tissues. The port is attached to a catheter (a thin, flexible tube) which provides fluid communication with a large blood vessel, such as the superior vena cava, in order to allow the injected fluid to dilute in the blood stream.

The implantation of a port is considered a minor procedure performed under local or general anesthesia by an interventional radiologist or surgeon. First, the surgeon achieve access to the desired vein, a skin incision is made afterwards in the access point. Second larger incision is made above the desired location of the port, through which a pocket-like subcutaneous void is made using blunt device. The catheter is extended subcutaneously between the two incisions using a blunt tunneler. One end of the catheter is then inserted into the vein and its other end is coupled to the port. Optionally, during deployment the catheter is cut to a desired length.

Besides progress made in past year in access ports design, there is still a need to develop ports and methods of implantation and deployment thereof, which are less traumatic and invasive, and simpler to perform, potentially also by non-surgical medical personnel.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

The present disclosure, in some embodiments thereof, relates to devices and methods for facilitating and/or improving repeated deliveries of fluids (e.g., fluids carrying nutrients, medicament and/or agents such as chemotherapy agents) into vasculature of a subject, and more particularly, but not exclusively, to vascular access ports and methods of delivery and deployment thereof in a body of a subject.

In certain embodiments, there is provided a vascular access port, comprising a port body coupled with a septum member covering a cavity defined by the port body, and a port body extension comprising a connection feature fixedly connectable to a portion of the port body.

In some embodiments, the vascular access port is selectively changeable subcutaneously from a delivery configuration wherein the port body and the port body extension are partially or wholly disengaged from each other, to a deployed configuration wherein the port body extension adjoins and is fixedly connected to the port body to form a unified structure of the vascular access port being greater in volume and/or in base area than the port body.

In some embodiments, the unified structure is greater in volume than the port body by at least 15%, optionally by at least 30%, In some embodiments, the unified structure has a lower surface area to volume ratio than the combined port body and port body extension when in the delivery configuration.

In some embodiments, the port body is configured to move distally towards the port body extension when the vascular access port changes to the deployed configuration.

In some embodiments, the vascular access port is configured to diminish a gap, formed between respective boundaries of the port body and the port body extension in the delivery configuration, when the vascular access port changes to the deployed configuration.

In some embodiments, the port body is configured to interlock with the port body extension when the vascular access port is in the deployed configuration.

In some embodiments, the port body extension includes a front edge pointing distally away from the port body and configured to cause atraumatic separation of tissue layers when forced to pass therebetween.

In some embodiments, the port body is configured to deform the port body extension, when the vascular access port changes to the deployed configuration.

In some embodiments, the port body extension is configured to expand laterally when the vascular access port changes to the deployed configuration.

In some embodiments, the port body extension is configured to expand laterally when a portion of the port body is pushed against an inner surface of the port body extension.

In some embodiments, the port body extension is deformable under force applicable by the port body thereto when the port body is pushed against the inner surface of the port body extension, such that the inner surface conforms at least partially to a shape imposed by an outer surface of the port body.

In some embodiments, the port body extension has lateral edges configured to shift laterally when the port body extension expands laterally, and to stretch, separate and/or dissect tissue layers when forced to pass therebetween.

In some embodiments, the port body is configured to maintain size and shape thereof when the vascular access port changes to the deployed configuration.

In some embodiments, the port body extension is configured to stabilize and/or fixate the port body in-place in a target implantation site in the subject body when the vascular access port changes to the deployed configuration.

In some embodiments, the port body extension is configured for insertion into a subcutaneous void separately from the port body when the vascular access port is in the delivery configuration, and to force increase is volume enclosed by the subcutaneous void by expanding therein when the vascular access port changes to the deployed configuration.

In some embodiments, the port body is configured to longitudinally interlock within the port body extension by way of longitudinally interengaging and/or interlocking edges.

In some embodiments, the unified structure is generally triangular shaped.

In some embodiments, the port body is generally triangular shaped.

In some embodiments, the port body has a inferior portion and a posterior portion, the inferior portion surrounds and/or encloses the cavity and the posterior portion includes or is connected to the septum member, wherein the port body extension includes an inner surface configured to engage and/or cover a front end and/or at least one side of the port body inferior portion, when the vascular access port is in the deployed configuration.

In some embodiments, when in the deployed configuration, the port body extension envelopes the front end and two opposing sides of the port body inferior portion.

In some embodiments, when in the deployed configuration, a rear end of the port body is not covered with the port body extension.

In some embodiments, the port body rear end is connected or connectable to a proximal end of a catheter for facilitating fluid communication between the cavity and a lumen of the catheter.

In some embodiments, the port body extension comprises of a plurality of interconnectable and/or detachable port body extension portions, wherein one of the port body extension portions is connected to a first side of the port body and another of the port body extension portions is connected to a second side of the port body when the vascular access port is in the deployed configuration.

In some embodiments, a base surface area of the unified structure is greater than a base surface area of the port body by at least 30%.

In certain embodiments, there is provided a method for deploying a vascular access port in a body of a subject, the method comprising:

>forming a subcutaneous void between or beneath skin tissue layers at a target implantation site in the subject body;

>inserting the vascular access port in a delivery configuration into the subcutaneous void, wherein the vascular access port includes a port body and a port body extension partially or wholly disengaged from each other; and >deploying the vascular access port by changing the vascular access port into the deployed configuration by adjoining and fixedly connecting the port body to the port body extension to form a unified structure of the vascular access port being greater in volume than the port body.

In some embodiments, the port body coupled with a septum member covering a cavity defined by the port body.

In some embodiments, the inserting results in the forming, or increases size of the subcutaneous void following the forming, by forcing the port body extension within the subject body through an incision.

In some embodiments, the deploying forces an increase in total volume enclosed by the subcutaneous void.

In some embodiments, the deploying includes forcing the port body extension to expand laterally by pushing a portion of the port body against an internal surface of the port body extension.

In some embodiments, the deploying includes forcing the port body extension to deform such that the internal surface at least partially conforms to a shape imposed by an external surface of the port body.

In some embodiments, the port body extension has lateral edges configured to shift laterally when the port body extension expands laterally, wherein the deploying includes stretching, separating or dissecting tissue layers forming the subcutaneous void with the lateral edges of the port body extension.

In some embodiments, the deploying includes stabilizing and/or fixating the port body in the subcutaneous void using the port body extension.

In some embodiments, the method further comprising:

>creating a subcutaneous surgical tunnel between a first incision and the target implantation site; and >delivering the vascular access port through the surgical tunnel to the subcutaneous void.

In some embodiments, the method further comprising:

>in vasculature of the subject, positioning a distal catheter end opened to a catheter lumen. In some embodiments, following the deploying, the cavity of the vascular access port is in fluid communication with the catheter lumen.

In some embodiments, the method further comprising:

>connecting a proximal catheter end, opened to the catheter lumen; to the port body so as to facilitate the fluid communication.

In some embodiments, the method further comprising:

>introducing the distal catheter end into the subject body via a second incision remote to a first incision;

>creating a subcutaneous surgical tunnel between the second incision and the first incision; and >delivering a proximal catheter end, opened to the catheter lumen, through the surgical tunnel towards the first incision.

In some embodiments, the inserting includes passing the port body extension and the port body through the surgical tunnel to the target implantation site.

In some embodiments, the passing is executed via a lumen of a port delivery apparatus extending along the surgical tunnel.

In some embodiments, the port delivery apparatus is configured functionally and/or structurally, at least in distal part thereof, to a surgical tunneler.

In some embodiments, the port delivery apparatus is configured to restrict motion of the port body relative to the port body extension in a chosen direction therealong.

In some embodiments, the port delivery apparatus is releasably connected to the port body and to the port body extension and includes a flat support member having a distal portion configured for supporting the port body extension and a sliding surface configured for supporting and facilitating unhindered sliding of the port body thereon.

In some embodiments, the deploying includes sliding the port body on the sliding surface until engaging with the port body extension and forcing the port body to adjoin and fixedly connect to the port body extension.

In some embodiments, the forming the subcutaneous void is executed using a distal end of the port delivery apparatus by pushing and/or manipulating the port delivery apparatus via a proximal end thereof.

In some embodiments, the creating the subcutaneous surgical tunnel is executed using a distal end of the port delivery apparatus by pushing and/or manipulating the port delivery apparatus via a proximal end thereof.

In some embodiments, the method further comprising:

>releasing the unified structure from the port delivery apparatus; and

>removing the port delivery apparatus from the surgical tunnel.

In some embodiments, the deploying includes diminishing a gap, formed between respective boundaries of the port body and the port body extension in the delivery configuration.

In some embodiments, the diminishing follows releasing the port body thereby allowing the port body to move distally towards the port body extension.

In certain embodiments, there is provided a subcutaneously implantable port body extension comprising: a tissue separation feature; a connection feature configured to fixedly connect to a portion of a port body to form a unified structure of a vascular access port; wherein the port body extension is configured for implantation prior to and separately from the port body.

In certain embodiments, there is provided a kit for implanting a vascular access port in a host, the kit comprising:

>a port body coupled with a septum member covering a cavity defined by the port body;

>a port body extension comprising a connection feature fixedly connectable to a portion of the port body; and >a port delivery apparatus releasably connectable to the port body and to the port body extension and configured for selectively changing the vascular access port from a delivery configuration wherein the port body and the port body extension are partially or wholly disengaged from each other, to a deployed configuration wherein the port body extension adjoins and is fixedly connected to the port body to form a unified structure of the vascular access port.

In some embodiments, the port delivery apparatus is configured to maintain a fixed gap formed between respective boundaries of the port body and the port body extension, when the vascular access port is in the delivery configuration.

In some embodiments, the port body is selectively slidable on a sliding surface of the port delivery apparatus towards and until engaging with the port body extension, when the vascular access port is in the delivery configuration.

In some embodiments, the port delivery apparatus includes at least one lateral barrier at a side of the sliding surface, extending along most or all length of the sliding surface, the at least one lateral barrier configured to restrict direction of motion of the port body to axial direction along the sliding surface, by continuously engaging a portion of the port body and preventing motions thereof in directions other than the axial direction during sliding of the port body along the sliding surface.

In some embodiments, the port body extension is fixedly connected to, and selectively releasable from, a distal portion of the port delivery apparatus.

In some embodiments, the port delivery apparatus includes an elongated delivery apparatus body.

In some embodiments, the delivery apparatus body includes a tissue penetrating front segment comprising a thin, flat support member having a distal portion configured for supporting the port body extension, and a sliding surface configured for supporting and facilitating unhindered sliding of the port body thereon.

In some embodiments, the tissue penetrating front segment is at least 4 cm in length.

In some embodiments, the tissue penetrating front segment includes a dissection tip configured for projecting distally relative to distal boundaries of the port body extension when attached to the delivery apparatus body.

In some embodiments, the dissection tip is at least 1 mm, optionally at least 5 mm, in length.

In some embodiments, the dissection tip is rounded along width and/or thickness thereof.

In some embodiments, the delivery apparatus body further includes a handle for manual manipulation of the tissue penetrating front segment.

In some embodiments, the port delivery apparatus includes a pusher slidably connected to the delivery apparatus body and selectively slidable along the tissue penetrating front segment, the pusher is configured to push the port body towards the port body extension sufficiently for engaging and connecting therebetween to form the unified structure of the vascular access port.

In some embodiments, the pusher includes a first actuator provided at a proximal portion thereof, the first actuator is provided in proximity to a proximal end of the tissue penetrating front segment when the vascular access port is in the delivery configuration.

In some embodiments, the tissue penetrating front segment includes a base member covering a bottom surface of the support member opposing the sliding surface, the base member includes a distal portion covering the distal portion of the support member and is coupled to at least one prong protruding therefrom through an opening on the distal portion of the support member.

In some embodiments, the at least one prong is configured to engage a mating recess in a bottom portion of the port body extension for facilitating fixation thereof to the port delivery apparatus.

In some embodiments, the port delivery apparatus includes a releasing element slidably connected to the delivery apparatus body and selectively slidable along the tissue penetrating front segment between the support member and the base member, wherein the releasing element is configured to separate the distal portion of the base member from the distal portion of the support member when a portion of the releasing element is provided therebetween, thereby retracting the at least one prong from the mating recess for releasing the port body extension from the port delivery apparatus.

In some embodiments, the releasing element includes a second actuator provided at a proximal portion thereof, the second actuator is provided in proximity to a proximal end of the tissue penetrating front segment when the vascular access port is in the delivery configuration.

In some embodiments, the kit further comprising a catheter connected or connectable to the port body for facilitating fluid communication between the cavity and a lumen enclosed by the catheter.

In certain embodiments, there is provided a kit for implanting a vascular access port in a host, the kit comprising:

>a port body comprising:

an inlet;

an outlet fluidly connected to the inlet; and a septum member covering the inlet;

>a port body extension configured to hold the port body when the port body and the port body extension are implanted for use;

>wherein the port body and the port body extension are unconnected or removably connected, wherein the port body extension can be implanted prior to the port body, and wherein the port body and the port body extension are subcutaneously connectable.

In some embodiments, the port body extension forms no part of the infusion functionality of the vascular access port.

In certain embodiments, there is provided a vascular access port, comprising a first port body member and a second port body member, interconnectable with each other and provided at least partially separated with each other, wherein joining of the first port body member with the second port body member forms a port body coupled with a septum member covering a cavity defined by the port body. In some embodiments, the first port body member entirely defines the cavity and/or directly connected to the septum member.

In certain embodiments, there is provided a vascular access port, comprising a first port body member and a second port body member, interconnectable with each other and provided at least partially separated with each other, wherein the first port body member entirely defines a cavity closed with a septum member.

In certain embodiments, there is provided a vascular access port, comprising a port body coupled with a septum member covering a cavity defined by the port body; the port body is provided in a delivery configuration, having an elongated form extending along a longitudinal axis, and is selectively changeable to a deployed configuration by changing in size parallel to the longitudinal axis.

In some embodiments, the port body changes in size by decreasing in length along the longitudinal axis.

In some embodiments, the vascular access port further comprising a port body appendix member connectable to the port body to form a unified structure being greater in length, width and/or height relative to the longitudinal axis than the port body in the delivery configuration.

In some embodiments, the port body is connectable to or includes an expandable element configured to increase size, area and/or volume of the vascular access port around the septum member when expanded. The expandable element may be selected from a group comprising of an inflatable member, a mesh, a preloaded elastic member, and a bellows shaped structure.

In some embodiments, the port body is further configured to change in size transversely to the longitudinal axis, when changing from the delivery configuration to the deployed configuration.

In some embodiments, the port body includes a first port body member and a second port body member interconnectable with each other and provided at least partially separated with each other when in the delivery configuration, the port body is configured to affect joining of the first port body member with the second port body member when changing to the deployed configuration.

In some embodiments, the first port body member is configured to longitudinally interlock within the second port body member by way of longitudinally interengaging and/or interlocking edges.

In certain embodiments, there is provided a method for deploying a vascular access port in a body of a subject. The method may include at least one of the following steps (not necessarily in same order):

>making an incision in proximity to a target implantation site in the subject body;

>forming a subcutaneous void between or beneath skin tissue layers at the target implantation site;

>inserting the vascular access port into the subcutaneous void, when the vascular access port includes a port body provided in a delivery configuration in an elongated form extending along a longitudinal axis, the port body is coupled with a septum member covering a cavity defined by the port body; and >deploying the vascular access port by changing the port body into the deployed configuration by decreasing size of the port body along the longitudinal axis.

In certain embodiments, there is provided a method for subcutaneously forming a vascular access port in a body of a subject. The method may include at least one of the following steps (not necessarily in same order):

>creating a subcutaneous surgical tunnel between an incision and a target implantation site;

>passing a first port body member and a second port body member through the surgical tunnel to the target implantation site;

>joining the first port body member with the second port body member thereby forming the vascular access port in a subcutaneous void at the target implantation site, the vascular access port includes a port body coupled with a septum member covering a cavity defined by the port body.

In some embodiments, passing a first port body member and a second port body member is executed via a lumen of an elongated delivery device extending along the surgical tunnel, optionally in a form of a surgical tunneler and/or restrict motion of the first and the second port body members to travelling along the rail.

In certain embodiments, there is provided an implant that includes:

>a first member enclosed with an external surface comprising a first member ridged edge and a first member grooved edge opposing the first member ridged edge, and a first member front located therebetween, the first member ridged edge has a longitudinally extending first ridge and the first member grooved edge has a longitudinally extending first groove;

>a second member enclosing an internal surface accessible through a rear opening provided on a second member rear, the internal surface comprising a second member ridged edge and a second member grooved edge opposing the second member ridged edge, the second member ridged edge has a longitudinally extending second ridge and the second member grooved edge has a longitudinally extending second groove;

>wherein the first member is configured to interlock longitudinally within the second member when pushed with the first member front through the rear opening and engaging the external surface of the first member with the internal surface of the second member, wherein the first ridge interengages longitudinally with the second groove and the second ridge interengages longitudinally with the first groove.

In some embodiments, the implant is configured such that by pushing the first member front through the rear opening and engaging the external surface with the internal surface, the internal surface is forced to expand until the internal surface corresponds in shape and/or size to the external surface.

In some embodiments, the implant is configured such that by pushing the first member front through the rear opening and engaging the external surface with the internal surface, the second member is forced to expand until the first member interlocks with the second member to a full extent.

In some embodiments, the second member is provided with the internal surface in a closed configuration wherein the second ridge interengages longitudinally and/or interlocks with the second groove, the implant is configured such that by pushing the first member front through the rear opening and engaging the external surface with the internal surface, the second ridge is forced to disengage from the second groove.

In some embodiments, the first groove is aligned, and corresponding in cross-section, to the second ridge and/or the second groove is aligned, and corresponding in cross-section, to the first ridge. In some embodiments, the first groove is aligned, and corresponding in cross-section, to the first ridge and/or the second groove is aligned, and corresponding in cross-section, to the second ridge.

In some embodiments, the first and second grooves and the first and second ridges share a corresponding cross-section comprising a wider head section and a narrow neck section, wherein, when the first ridge interengages longitudinally with the second groove and the second ridge interengages longitudinally with the first groove, the head section of the first and second ridges cross section nests within the head section, and held in place by the neck section, of the respective first and second grooves cross section.

In some embodiments, the first member entirely defines a cavity closed with a septum member.

In certain embodiments, there is provided a method for assembling an implant in a target location in a body of a subject, the method comprising one or more of the followings (not necessarily in same order):

>providing a first member and a second member in the target location, the first member is enclosed with an external surface comprising a first member ridged edge and a first member grooved edge opposing the first member ridged edge, and a first member front located therebetween, the second member enclosing an internal surface accessible through a rear opening provided on or formed by a second member rear, the internal surface comprising a second member ridged edge and a second member grooved edge opposing the second member ridged edge, the first member ridged edge has a longitudinally extending first ridge, the first member grooved edge has a longitudinally extending first groove, the second member ridged edge has a longitudinally extending second ridge and the second member grooved edge has a longitudinally extending second groove;

>pushing the first member front through the rear opening to engage the external surface of the first member with the internal surface of the second member;

>longitudinally interengaging the first ridge with the second groove and the second ridge with the first groove; and >interlocking the first member longitudinally within the second member.

In some embodiments, the pushing of the first member includes forcing the internal surface to expand until the internal surface corresponds in shape and/or size to the external surface.

In some embodiments, the pushing of the first member includes forcing the second member to expand until the first member interlocks with the second member to a full extent.

In some embodiments, the pushing of the first member includes forcing the second member to expand until the implant reached a predetermined size and/or shape.

In some embodiments, the second member is provided with the internal surface in a closed configuration wherein the second ridge interengages longitudinally and/or interlocks with the second groove, wherein the pushing includes forcing the second ridge to disengage from the second ridge.

In certain embodiments, there is provided a method for deploying a vascular access port in a body of a subject, the method comprising:

>inserting a port body of the vascular access port into a target implantation site in the subject body, such that a posterior portion of the port body is accessible to repeated fluid transfer access;

>in the target implantation site, compacting tissue mass surrounding periphery of the port body thereby increasing a volume of a void formed in the target implantation site between the periphery of the port body and the compacted tissue mass; and >occupying the increased void volume with the vascular access port, wherein the vascular access port is greater in volume than the port body.

In some embodiments, an inferior portion of the port body defines a cavity and the posterior portion of the port body is coupled with a septum member covering the cavity.

In some embodiments, the compacted tissue mass surrounds only an inferior portion of the port body located inferiorly to the posterior portion.

In some embodiments, the void is a subcutaneous void located between or beneath skin tissue layers at the target implantation site.

In some embodiments, the method further includes inserting the vascular access port in a delivery configuration into the void wherein the vascular access port includes a port body extension partially or wholly disengaged from the port body.

In some embodiments, the inserting forms the void by forcing the port body extension within the subject body through an incision.

In some embodiments, the occupying includes changing the vascular access port into a deployed configuration by adjoining and fixedly connecting the port body to the port body extension to form a unified structure of the vascular access port being greater in volume than the port body.

In some embodiments, the changing includes forcing the port body extension to expand laterally by pushing a portion of the port body against an internal surface of the port body extension.

In some embodiments, the occupying includes expanding a portion of the port body.

Furthermore, and by way of example without limitation, the inventions disclosed herein include at least the following seventy-seven embodiments:

1, A vascular access port, comprising:

a port body coupled with a septum member covering a cavity defined by the port body; and a port body extension comprising a connection feature fixedly connectable to a portion of the port body;

the vascular access port is selectively changeable subcutaneously from a delivery configuration wherein the port body and the port body extension are partially or wholly disengaged from each other, to a deployed configuration wherein the port body extension adjoins and is fixedly connected to the port body to form a unified structure of the vascular access port being greater in volume and/or in base area than the port body.

2. The vascular access port of embodiment 1, wherein the unified structure is greater in volume than the port body by at least 15%.

3. The vascular access port of any preceding embodiment, wherein the unified structure has a lower surface area to volume ratio than the combined port body and port body extension when in the delivery configuration.

4. The vascular access port of any preceding embodiment, wherein the port body is configured to move distally towards the port body extension when the vascular access port changes to the deployed configuration.

5. The vascular access port of any preceding embodiment, configured to diminish a gap, formed between respective boundaries of the port body and the port body extension in the delivery configuration, when the vascular access port changes to the deployed configuration.

6. The vascular access port of any preceding embodiment, wherein the port body is configured to interlock with the port body extension when the vascular access port is in the deployed configuration.

7. The vascular access port of any preceding embodiment, wherein the port body extension includes a front edge pointing distally away from the port body and configured to cause atraumatic separation of tissue layers when forced to pass therebetween.

8. The vascular access port of any preceding embodiment, wherein the port body is configured to deform the port body extension, when the vascular access port changes to the deployed configuration.

9. The vascular access port of any preceding embodiment, wherein the port body extension is configured to expand laterally when the vascular access port changes to the deployed configuration.

10. The vascular access port of any preceding embodiment, wherein the port body extension is configured to expand laterally when a portion of the port body is pushed against an inner surface of the port body extension.

11. The vascular access port of any preceding embodiment, wherein the port body extension is deformable under force applicable by the port body thereto when the port body is pushed against the inner surface of the port body extension, such that the inner surface conforms at least partially to a shape imposed by an outer surface of the port body.

12. The vascular access port of any preceding embodiment, wherein the port body extension has lateral edges configured to shift laterally when the port body extension expands laterally, and to stretch, separate and/or dissect tissue layers when forced to pass therebetween.

13. The vascular access port of any preceding embodiment, wherein the port body is configured to maintain size and shape thereof when the vascular access port changes to the deployed configuration.

14. The vascular access port of any preceding embodiment, wherein the port body extension is configured to stabilize and/or fixate the port body in-place in a target implantation site in the subject body when the vascular access port changes to the deployed configuration.

15. The vascular access port of any preceding embodiment, wherein the port body extension is configured for insertion into a subcutaneous void separately from the port body when the vascular access port is in the delivery configuration, and to force increase is volume enclosed by the subcutaneous void by expanding therein when the vascular access port changes to the deployed configuration.

16. The vascular access port of any preceding embodiment, wherein the port body is configured to longitudinally interlock within the port body extension by way of longitudinally interengaging and/or interlocking edges.

17. The vascular access port of any preceding embodiment, wherein the unified structure is generally triangular shaped.

18. The vascular access port of any preceding embodiment, wherein the port body is generally triangular shaped.

19. The vascular access port of any preceding embodiment, wherein the port body has an inferior portion and a posterior portion, the inferior portion surrounds the cavity and the posterior portion is connected to the septum member, wherein the port body extension includes an inner surface configured to engage and/or cover a front end and/or at least one side of the port body inferior portion, when the vascular access port is in the deployed configuration.

20. The vascular access port of embodiment 19, wherein, when in the deployed configuration, the port body extension envelopes the front end and two opposing sides of the port body inferior portion.

21. The vascular access port of any preceding embodiment, wherein, when in the deployed configuration, a rear end of the port body is not covered with the port body extension.

22. The vascular access port of embodiment 21, wherein the port body rear end is connected or connectable to a proximal end of a catheter for facilitating fluid communication between the cavity and a lumen of the catheter.

23. The vascular access port of any preceding embodiment, wherein the port body extension comprises of a plurality of interconnectable and/or detachable port body extension portions, wherein one of the port body extension portions is connected to a first side of the port body and another of the port body extension portions is connected to a second side of the port body when the vascular access port is in the deployed configuration.

24. The vascular access port of any preceding embodiment, wherein a base surface area of the unified structure is greater than a base surface area of the port body by at least 30%.

25. A method for deploying a vascular access port in a body of a subject, the method comprising:

forming a subcutaneous void between or beneath skin tissue layers at a target implantation site in the subject body;

inserting the vascular access port in a delivery configuration into the subcutaneous void, wherein the vascular access port includes a port body and a port body extension partially or wholly disengaged from each other; and deploying the vascular access port by changing the vascular access port into a deployed configuration by adjoining and fixedly connecting the port body to the port body extension to form a unified structure of the vascular access port being greater in volume than the port body.

26. The method of embodiment 25, wherein the port body coupled with a septum member covering a cavity defined by the port body.

27. The method of any one of embodiments 25 or 26, wherein the inserting results in the forming, or increases size of the subcutaneous void following the forming, by forcing the port body extension within the subject body through an incision.

28. The method of any one of embodiments 25 through 27, wherein the deploying forces an increase in total volume enclosed by the subcutaneous void.

29. The method of any one of embodiments 25 through 28, wherein the deploying includes forcing the port body extension to expand laterally by pushing a portion of the port body against an internal surface of the port body extension.

30. The method of any one of embodiments 25 through 29, wherein the deploying includes forcing the port body extension to deform such that the internal surface at least partially conforms to a shape imposed by an external surface of the port body.

31. The method of any one of embodiments 25 through 30, wherein the port body extension has lateral edges configured to shift laterally when the port body extension expands laterally, wherein the deploying includes stretching, separating or dissecting tissue layers forming the subcutaneous void with the lateral edges of the port body extension.

32. The method of any one of embodiments 25 through 31, wherein the deploying includes stabilizing and/or fixating the port body in the subcutaneous void using the port body extension.

33. The method of any one of embodiments 25 through 32, further comprising:

creating a subcutaneous surgical tunnel between a first incision and the target implantation site; and delivering the vascular access port through the surgical tunnel to the subcutaneous void.

34. The method of any one of embodiments 25 through 33, further comprising:

in vasculature of the subject, positioning a distal catheter end opened to a catheter lumen;

wherein, following the deploying, the cavity of the vascular access port is in fluid communication with the catheter lumen.

35. The method of embodiment 34, further comprising connecting a proximal catheter end, opened to the catheter lumen, to the port body so as to facilitate the fluid communication.

36. The method of embodiment 34, method further comprising:

introducing the distal catheter end into the subject body via a second incision remote to a first incision;

creating a subcutaneous surgical tunnel between the second incision and the first incision; and delivering a proximal catheter end, opened to the catheter lumen, through the surgical tunnel towards the first incision.

37. The method of embodiment 36, wherein the inserting includes passing the port body extension and the port body through the surgical tunnel to the target implantation site.

38. The method of embodiment 37, wherein the passing is executed via a lumen of a port delivery apparatus extending along the surgical tunnel.

39. The method of embodiment 38, wherein the port delivery apparatus is configured functionally and/or structurally, at least in distal part thereof, to a surgical tunneler.

40. The method of embodiment 38, wherein the port delivery apparatus is configured to restrict motion of the port body relative to the port body extension in a chosen direction therealong.

41. The method of embodiment 38, the port delivery apparatus is releasably connected to the port body and to the port body extension and includes a flat support member having a distal portion configured for supporting the port body extension and a sliding surface configured for supporting and facilitating unhindered sliding of the port body thereon; wherein the deploying includes sliding the port body on the sliding surface until engaging with the port body extension and forcing the port body to adjoin and fixedly connect to the port body extension.

42. The method of embodiment 41, wherein the forming the subcutaneous void is executed using a distal end of the port delivery apparatus by pushing and/or manipulating the port delivery apparatus via a proximal end thereof.

43. The method of embodiment 41, wherein the creating the subcutaneous surgical tunnel is executed using a distal end of the port delivery apparatus by pushing and/or manipulating the port delivery apparatus via a proximal end thereof.

44. The method of embodiment 41, further comprising releasing the unified structure from the port delivery apparatus; and removing the port delivery apparatus from the surgical tunnel.

45. The method of any one of embodiments 25 through 44, wherein the deploying includes diminishing a gap, formed between respective boundaries of the port body and the port body extension in the delivery configuration.

46. The method of embodiment 45, wherein the diminishing follows releasing the port body thereby allowing the port body to move distally towards the port body extension.

47. A subcutaneously implantable port body extension comprising:

a tissue separation feature;

a connection feature configured to fixedly connect to a portion of a port body to form a unified structure of a vascular access port;

wherein the port body extension is configured for implantation prior to and separately from the port body.

48. A kit for implanting a vascular access port in a host, the kit comprising:

a port body comprising:

an inlet;

an outlet fluidly connected to the inlet; and a septum member covering the inlet;

a port body extension configured to hold the port body when the port body and the port body extension are implanted for use;

wherein the port body and the port body extension are unconnected or removably connected, wherein the port body extension can be implanted prior to the port body, and wherein the port body and the port body extension are subcutaneously connectable.

49. The kit of embodiment 48, wherein the port body extension forms no part of the infusion functionality of the vascular access port.

50. A kit for implanting a vascular access port in a host, the kit comprising:

a port body coupled with a septum member covering a cavity defined by the port body;

a port body extension comprising a connection feature fixedly connectable to a portion of the port body; and a port delivery apparatus releasably connectable to the port body and to the port body extension and configured for selectively changing the vascular access port from a delivery configuration wherein the port body and the port body extension are partly or wholly disengaged from each other, to a deployed configuration wherein the port body extension adjoins and is fixedly connected to the port body to form a unified structure of the vascular access port.

51. A kit according to embodiment 50, wherein the port delivery apparatus is configured to maintain a fixed gap formed between respective boundaries of the port body and the port body extension, when the vascular access port is in the delivery configuration.

52. A kit according to any one of embodiments 50 or 51, wherein the port body is selectively slidable on a sliding surface of the port delivery apparatus towards and until engaging with the port body extension, when the vascular access port is in the delivery configuration.

53. A kit according to any one of embodiments 50 through 52, wherein the port delivery apparatus includes at least one lateral barrier at a side of the sliding surface, extending along most or all length of the sliding surface, the at least one lateral barrier configured to restrict direction of motion of the port body to axial direction along the sliding surface, by continuously engaging a portion of the port body and preventing motions thereof in directions other than the axial direction during sliding of the port body along the sliding surface.

54. A kit according to any one of embodiments 50 through 53, wherein the port body extension is fixedly connected to, and selectively releasable from, a distal portion of the port delivery apparatus.

55. A kit according to any one of embodiments 50 through 54, wherein the port delivery apparatus includes an elongated delivery apparatus body.

56. A kit according to embodiment 55, wherein the delivery apparatus body includes a tissue penetrating front segment comprising a thin, flat support member having a distal portion configured for supporting the port body extension, and a sliding surface configured for supporting and facilitating unhindered sliding of the port body thereon.

57. A kit according to embodiment 56, wherein the tissue penetrating front segment is at least 4 cm in length.

58. A kit according to embodiment 56, wherein the tissue penetrating front segment includes a dissection tip configured for projecting distally relative to distal boundaries of the port body extension when attached to the delivery apparatus body.

59. A kit according to embodiment 58, wherein the dissection tip is at least 1 mm, optionally at least 5 mm, in length.

60. A kit according to embodiment 58, wherein the dissection tip is rounded along width and/or thickness thereof.

61. A kit according to embodiment 56, wherein the delivery apparatus body further includes a handle for manual manipulation of the tissue penetrating front segment.

62. A kit according to embodiment 56, wherein the port delivery apparatus includes a pusher slidably connected to the delivery apparatus body and selectively slidable along the tissue penetrating front segment, the pusher is configured to push the port body towards the port body extension sufficiently for engaging and connecting therebetween to form the unified structure of the vascular access port.

63. A kit according to embodiment 62, wherein the pusher includes a first actuator provided at a proximal portion thereof, the first actuator is provided in proximity to a proximal end of the tissue penetrating front segment when the vascular access port is in the delivery configuration.

64. A kit according to embodiment 56, wherein the tissue penetrating front segment includes a base member covering a bottom surface of the support member opposing the sliding surface, the base member includes a distal portion covering the distal portion of the support member and is coupled to at least one prong protruding therefrom through an opening on the distal portion of the support member.

65. A kit according to embodiment 64, wherein the at least one prong is configured to engage a mating recess in a bottom portion of the port body extension for facilitating fixation thereof to the port delivery apparatus.

66. A kit according to embodiment 65, wherein the port delivery apparatus includes a releasing element slidably connected to the delivery apparatus body and selectively slidable along the tissue penetrating front segment between the support member and the base member, wherein the releasing element is configured to separate the distal portion of the base member from the distal portion of the support member when a portion of the releasing element is provided therebetween, thereby retracting the at least one prong from the mating recess for releasing the port body extension from the port delivery apparatus.

67. A kit according to embodiment 66, wherein the releasing element includes a second actuator provided at a proximal portion thereof, the second actuator is provided in proximity to a proximal end of the tissue penetrating front segment when the vascular access port is in the delivery configuration.

68. A kit according to any one of embodiments 50 through 67, further comprising a catheter connected or connectable to the port body for facilitating fluid communication between the cavity and a lumen enclosed by the catheter.

69. A method for deploying a vascular access port in a body of a subject, the method comprising:

inserting a port body of the vascular access port into a target implantation site in the subject body, such that a posterior portion of the port body is accessible to repeated fluid transfer access;

in the target implantation site, compacting tissue mass surrounding periphery of the port body thereby increasing a volume of a void formed in the target implantation site between the periphery of the port body and the compacted tissue mass; and occupying the increased void volume with the vascular access port, wherein the vascular access port is greater in volume than the port body.

70. A method according to embodiment 69, wherein an inferior portion of the port body defines a cavity and the posterior portion of the port body is coupled with a septum member covering the cavity.

71. A method according to any one of embodiments 69 or 70, wherein the compacted tissue mass surrounds only an inferior portion of the port body located inferiorly to the posterior portion.

72. A method according to any one of embodiments 69 through 71, wherein the void is a subcutaneous void located between or beneath skin tissue layers at the target implantation site.

73. A method according to any one of embodiments 69 through 72, further includes inserting the vascular access port in a delivery configuration into the void wherein the vascular access port includes a port body extension partially or wholly disengaged from the port body.

74. The method according to embodiment 73, wherein the inserting forms the void by forcing the port body extension within the subject body through an incision.

75. A method according to embodiment 73, wherein the occupying includes changing the vascular access port into a deployed configuration by adjoining and fixedly connecting the port body to the port body extension to form a unified structure of the vascular access port being greater in volume than the port body.

76. The method according to embodiment 75, wherein the changing includes forcing the port body extension to expand laterally by pushing a portion of the port body against an internal surface of the port body extension.

77. The method according to any one of embodiments 69 through 76, wherein the occupying includes expanding a portion of the port body.

All technical or/and scientific words, terms, or/and phrases, used herein have the same or similar meaning as commonly understood by one of ordinary skill in the art to which the invention pertains, unless otherwise specifically defined or stated herein. Exemplary embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

DETAILED DESCRIPTION

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

The present disclosure, in some embodiments thereof, relates to devices and methods for facilitating and/or improving repeated deliveries of fluids (e.g., fluids carrying nutrients, medicament and/or agents such as chemotherapy agents) into vasculature of a subject, and more particularly, but not exclusively, to vascular access ports and methods of delivery and deployment thereof in a body of a subject. In some embodiments, vascular access ports of the present disclosure can improve safety and/or efficacy of the surgical implantation procedure of access port and catheter by reducing size or number of surgical processes (like cuts, incisions, and tunneling), their duration and/or complexity, thereby also provide a less traumatic experience and easier recovery for the patient.

Figure 1A:
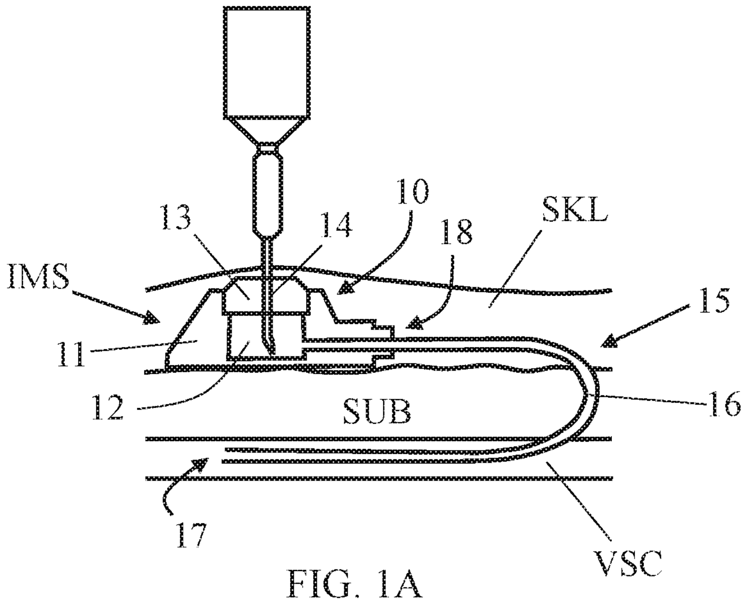
FIGS. 1A-1B schematically illustrate respectively a side cross-sectional view and a top cross-sectional view of an exemplary deployed vascular access port, in accordance with some embodiments.
Figure 1B:
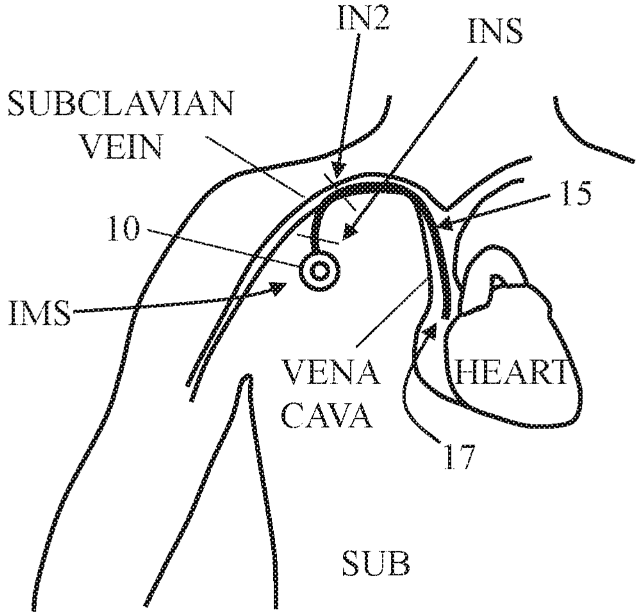

FIGS. 1A-1B schematically illustrate respectively a side cross-sectional view and a top cross-sectional view of an exemplary vascular access port 10 in a deployed configuration. Port 10 is implanted in a target implantation site IMS subcutaneously beneath skin layers SKL (including optionally within or beneath fat tissue) in a subject SUB. Vascular access port 10 includes a port body 11 defining a cavity 12 and coupled with a septum 13 that covers and seals cavity 12 from surroundings. Septum 13 is configured for repeated puncturing of needles, like needle 14 shown in FIG. 1A, without compromising sealing of cavity 12 during needle placement therethrough and after the needle is withdrawn.

"Repeated" in this context may refer to more than 10 consecutive needle punctures, optionally more than 100 consecutive needle punctures, optionally more than 1,000 consecutive needle punctures, optionally more than 10,000 consecutive needle punctures, or higher or lower. "Needle" in this context may refer to needles approved for fluid deliveries through vascular access ports, such as for intravenous administration.

When fully deployed, vascular access port 10 has cavity 12 in fluid communication with vasculature VSC of subject SUB, normally a large blood vessel such as the Subclavian vein or the Vena Cava, so that fluid administrated into cavity 12 via needle 14 will flow directly to the subject's vascular system. A catheter 15 with catheter lumen 16 has a first catheter end 17 thereof positioned in and opened to vasculature VSC, and a second catheter end 18 thereof is connected to port body 11 and opened to cavity 12; catheter ends, 17 and 18, are opened to catheter lumen 16 and facilitate fluid communication between cavity 12 and vasculature VSC. FIG. 1B shows an optional deployment scheme where port 10 is positioned on an upper part the subject's chest in proximity to access opening made to Jugular vein, with first catheter end 17 positioned in the Vena Cava in proximity to subjects right atrium. Vascular access port 10 may be provided separately to catheter 15 with a connector configured for selective connection therebetween, optionally within the body, or alternatively vascular access port 10 and catheter 15 are provided together as an assembly kit or as a unified device.

As used herein, the term "vascular access port" refers to one or more implantable components that together are intended for use after their implantation to repeatedly transfer fluids administered to and/or withdrawn from a subject. The disclosures described herein are advantageous also when used in conjunction with vascular access ports that have a septum configured for repeated puncturing by a needle, but this particular feature is not a requirement and other forms of needle access openings or platforms may apply. Some vascular access ports described herein include one or more components configured, collectively, when properly assembled and deployed, for prolonged implantation in a live (e.g., human) subject and for repeated fluid transfer access, such as through a septum. The vascular access port includes at least a structural object referred to herein as a "port body" which serves as a facilitating structure for fluid transfer access and/or as a support structure configured for holding components (e.g., a septum) applicable for fluid transfer access. In some embodiments, the port body forms a cavity beneath (e.g., inferiorly to) the needle access opening or septum, which is sized and shaped for repeatedly receiving a needle tip, for accumulating a chosen or predetermined volume of fluid (e.g., a liquid such as a solution, a suspension or a colloid), and/or for fluid administration to, and/or withdrawal from, a vasculature of the live subject. Before or after implantation, a catheter may be attached to the vascular access port with a distal end that physically enters the vasculature of the patient. Once connected, a lumen of the catheter is provided in direct fluid communication with the port body cavity. A "vascular access port" as described herein, or a kit comprising it, may include or not include such a catheter and may include or not include a fitting for such a catheter. A vascular access port may be referred to herein as simply a "port" or an "implant". A vascular access port may have additional components and functionality not associated with fluid delivery or withdrawal.

The port body may be structurally and/or functionally configured for facilitating at least the basic function of the vascular access port of repeated accumulating and delivering and/or withdrawing fluid to or from subject's vasculature, and it may optionally lack or be initially configured without one or more other features, optional or vital ones, for facilitating additional functions associated with delivery, deployment and/or prolonged use of a vascular access port. The port body may be connected to at least one other component for providing the vascular access port additional features or capabilities, for example improved or easier deliverability, selective fixation to body tissues surrounding the port body and/or increased stability in a chosen implantation site such as a preformed subcutaneous void.

In some embodiments, the port body itself must be changed or reconfigured (such as by way of reshaping or expanding portions thereof, or by assembling the port body from sub-components thereof) before or during deployment of the vascular access port. Such changes of the port body and/or of the vascular access port may be accomplished within the body of the subject, optionally in a subcutaneous location in the body (e.g., beneath one or more layers of the subject's skin).

The term "port body" may refer to one or more components out of a plurality of components forming the vascular access port, or it may refer to the collection of these components that together are configured to form a vascular access port. The term "port body" may also refer to only the component of a complete port body that contains the part of a vascular access port configured for fluid transfer access and/or delivery and withdrawal. For example, a "port body" may be referred to as only the septum containing or holding component, the cavity forming component, and/or the catheter connecting component, of a complete port body for a vascular access port.

When deployed to form a vascular access port suitable for use in fluid delivery or withdrawal, the coupled/engaged collection of port body components, including the "port body" or components thereof, may be referred to herein as a "unified structure" of the vascular access port. Prior to deployment, these components may be fully engaged, fully disengaged, or partially disengaged, and this may include for example being unconnected with each other, easily movable one relative to the other, and/or separated from each other with or without a gap therebetween. The coupling or engagement functionality may be provided by all or some or only one of the separable port body components. The components of a port body may be referred to herein generically such as the first port body member and second port body member, etc. In some embodiments, components of the vascular access port, other than the port body, are designated with other functional associations such as "port body extension." Of course, descriptive functional or structural designations could be applied to each part of a multi-component port body such as "second member", "septum support," "expander," "retainer," "base," or the like.

Deploying the vascular access includes at least inserting the port body into a target implantation site in the subject body, such that a posterior portion of the port body is accessible to repeated fluid transfer access. Vascular access port deployment then includes compacting of tissue mass surrounding periphery of the port body thereby increasing a volume of a void formed in the target implantation site between the periphery of the port body and the compacted tissue mass. The void can be a subcutaneous void located between or beneath skin tissue layers at the target implantation site. Concurrently with increasing the void volume, or immediately afterwards, the increased void volume is occupied with the vascular access port such as by increasing the volume of the port body or by connecting one or more solid shaped components (e.g., a port body extension) thereto. This also includes the situation that the tissue mass compaction may be a direct result of such increase in port body volume. The compacted tissue mass normally affects a continuous pressure on the deployed vascular access port and thereby increase its fixation and/or stability in the subcutaneous void. The port body may include an inferior portion which defines a cavity and a posterior portion coupled with a septum member covering the cavity, and the vascular access port may be deployed such that the compacted tissue mass surrounds only an inferior portion and not the posterior portion of the port body.

The vascular access port is optionally inserted to the target implantation site (e.g., into the void) when provided in a delivery configuration, wherein a port body extension thereof is partially or wholly disengaged from the port body, and occupying the increased void volume is accomplished by changing (e.g., transferring) the vascular access port into a deployed configuration wherein the port body and the port body extension are forced to adjoin and fixedly connect to form a unified structure of the vascular access port being greater in volume than the port body. Optionally and alternatively, a portion of the port body can be expanded to occupy (and optionally form) the increased void volume.

Figure 2A:
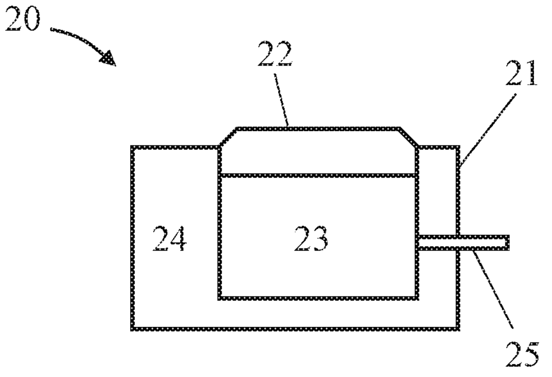
FIGS. 2A-2C schematically illustrate respectively side cross-sectional view and top views of an exemplary subcutaneously formable vascular access port, in accordance with some embodiments.
Figure 2B:
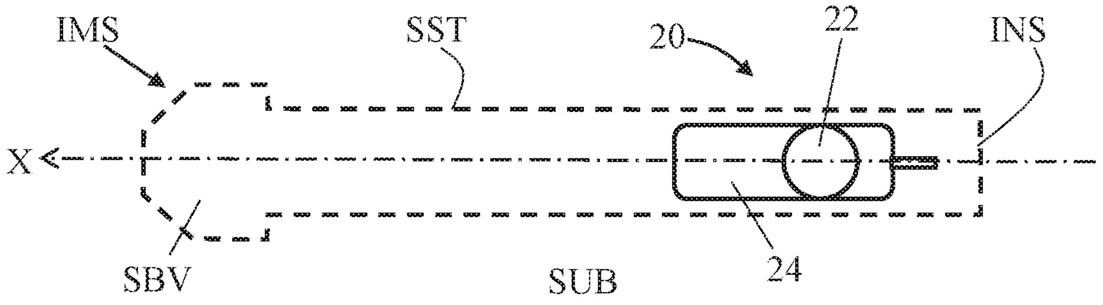
Figure 2C:
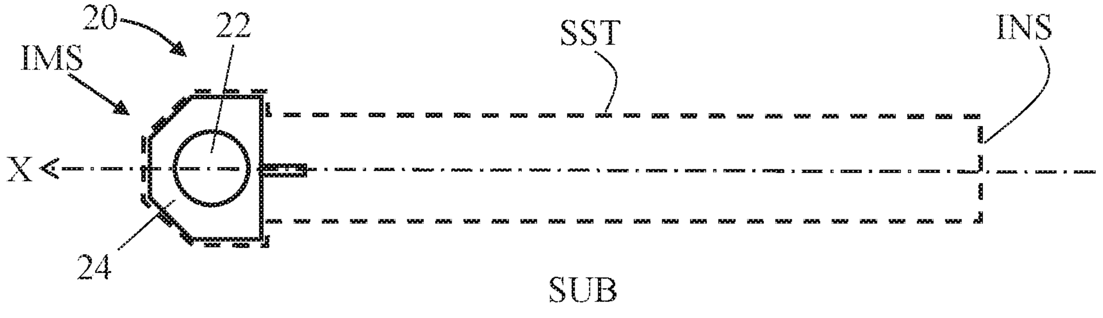

Reference is made to FIGS. 2A-2C which schematically illustrate respectively side cross-sectional view and top views of an exemplary subcutaneously formable vascular access port 20. Port 20 may be configured same or similar in function and/or structure to port 10 in terms of its fluid delivery aspects, and/or placed into the proximal portion of the incision similarly thereto, with or without catheter 15.

Port 20 includes a port body 21 coupled with a septum member 22 covering a cavity 23 defined by port body 21. Port body 21 is provided in a delivery configuration (shown in FIGS. 2A and 2B), having an elongated form extending along a longitudinal axis X, and is selectively changeable to a deployed configuration (as shown in FIG. 2C) by changing in size parallel to the longitudinal axis X. Change in size may be achieved by decreasing in length along longitudinal axis X, optionally from a first predetermined length to a second, smaller, predetermined length. Port body 21 is further configured to change in size transversely to the longitudinal axis X, when changing from the delivery configuration to the deployed configuration.

Figure 8A:
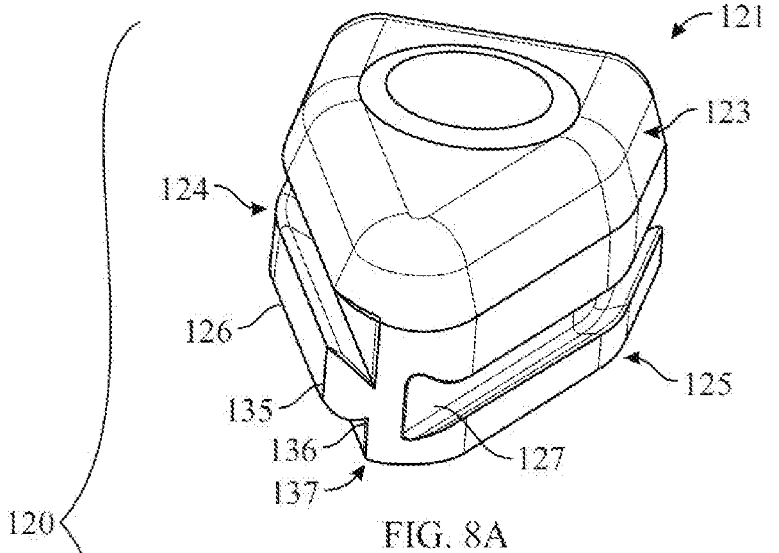
FIGS. 8A-8E schematically illustrate isometric views of a second exemplary implant comprising a first and a second members with interlocking edges, in accordance with some embodiments.

Port body 21 is connectable to or includes an expandable element or portion 24 that is configured to increase size, area and/or volume of vascular access port 20 around septum member 22 when expanded, as shown in FIG. 2C. Expandable element or portion may include or be configured as an inflatable member, a mesh, a preloaded elastic member, or a bellows shaped structure. A port body component providing this functionality may be referred to herein as a "port body extension" or "expander." Port body 21 may expand or increase in cross section or volume by way of self-expansion or deformation, or by connecting with one or more appendix members connectable thereto to form a unified structure being greater in length, width and/or height than the port body alone in the delivery configuration. In some such embodiments, port body 21 is connectable to a port body extension (as will be described with respect to vascular access port 100) to form a unified structure having a final shape and size. The port body 21 either before or after deployment may be configured in an essentially unlimited variety of flat or curved solid shapes such as prisms, pyramids, cubes, spheres, ellipsoids, ovoids, and the like, in any combination thereof, either alone or as augmentations to other shapes. In some embodiments, the final shape of vascular access port 20, if as a unified structure or in its basic structure, is generally triangular as defined by side periphery thereof. The phrase "generally triangular," as used herein, encompasses any generally three-sided geometry wherein adjacent sides intersect, including but not limited to regular or irregular polyhedron and/or curved solid with one or more three edge bound faces. The term "generally triangular" may include shapes with rounded edges, curved faces, and other deviations from linear and planar geometric components, for example three-sided polygons, circular triangles and equilateral triangles. For example, the wedge shapes shown in FIGS. 5C, 8A and 8E discussed below are examples of generally triangular shaped ports. Port body 21 may include a single cavity or several distinct cavities, covered with one or several distinct septum members, provided as a single element or as several interconnectable members.

For deploying vascular access port 20 in a body of a subject (e.g., subject SUB), an incision INS is made in proximity to a target implantation site (e.g., implantation site IMS) in the subject body. A subcutaneous void SBV (e.g., in a form of pocket) is formed between or beneath skin tissue layers (e.g., skin tissue layers SKL) at target implantation site IMS. Vascular access port 20 is inserted into the subcutaneous void SBV when port body 21 is provided in the delivery configuration (FIG. 2B). Vascular access port 20 is then deployed by changing port body 21 into the deployed configuration by decreasing its size along longitudinal axis X (FIG. 2C). The subcutaneous void SBV may be initially formed, or increased in size, as a result of inserting port 20 by forcing port body 21 within the subject body through incision INS. Increasing size of subcutaneous void SBV can result in compaction of tissue mass surrounding port body 21, thereby increasing fixation and/or stability of port 20 in the target implantation site IMS.

As part of port 20 deployment, or as a distinct step, catheter 15 is provided and implanted for providing fluid communication between cavity 23 and vasculature VSC of subject SUB (similarly to as shown in FIGS. 1A and 1B and as described above).

Optionally, a subcutaneous surgical tunnel SST is created between incision INS and target implantation site IMS, and port 20 is delivered through the surgical tunnel SST to the subcutaneous void SBV, and optionally no other incision is made for port (and catheter) deployment. Optionally and alternatively, incision INS is located at the surface of, and serves as opening directly into, implantation site IMS, without having a surgical tunnel extending and connecting therebetween. In some such embodiments, first catheter end 17 is inserted into the subject body via a second incision IN2 remote to incision INS (as shown in FIG. 1B), and subcutaneous surgical tunnel SST is created between second incision IN2 and incision INS. Optionally, second catheter end 18 is delivered through the surgical tunnel SST towards from second incision IN2 to incision INS if for connecting with port 20 already present in subcutaneous void SBV (e.g., by coupling with a connector 25), or already connected with port 20 and delivered together therewith to implantation site IMS.

The embodiment shown in FIGS. 2A-2C illustrates some general principles of many advantageous embodiments of vascular access ports described herein. One advantageous feature is that the ratio of the externally exposed surface area to the total enclosed volume of the originally delivered components of the vascular access port may be lower in the deployed configuration than in the delivery configuration. This change in geometry is very different from vascular access port stabilization methods that use spikes or plates or other projections that are made to extend outward from the port body portion containing the septum. While these may be somewhat beneficial, improvement in port stability is much greater when the total unified structure changes geometry to decrease surface area to volume ratio rather than increase it as spikes or plates will do.

A reduction in surface area to volume ratio upon deployment can be accomplished in a variety of ways. In some embodiments, the shape can stay substantially the same when deployed but the dimensions can increase, such as described above where an expandable element 24 may be provided around the port body portion with the septum, Another approach can be to change the shape of the vascular access port to distribute the volume more evenly in all three spatial dimensions. This occurs, for example, in the shape transition from FIG. 2B to 2C discussed above. In other embodiments, such as shown in FIGS. 3 through 8, the reduction in surface area to volume ratio may be accomplished by engaging upon deployment substantial segments of the surface areas of two or more components of the vascular access port that are delivered in a disengaged or only partially engaged state. This reduces the externally exposed surface area of the unified structure without reducing the sum total enclosed volume of the components. The embodiments described below with reference to FIGS. 5, 7, and 8 are especially advantageous forms of this approach because the process of engaging (also referred to herein as interlocking, adjoining, interconnecting) surface areas of the components also expands the base width of the vascular access port components. This further enhances the fixation and stability of the vascular access port within the implantation site IMS.

Independent of any changes in surface area to volume ratio between delivery and deployed configurations, in some embodiments the volume of the structure after deployment is significantly larger than the volume of any of the one or more delivered components prior to deployment. As discussed above, this allows the deployed configuration to become solidly affixed in the implantation site IMS. One way of accomplishing this is utilizing an expandable portion such as portion 24 of FIG. 2. Also, as shown and discussed below with respect at least to FIGS. 3 through 8, this volume increase may be accomplished by engaging two components of a port body that are wholly or partially disengaged in the delivery configuration. Another aspect of the change from delivery to deployed configuration may be an increase in base area of the deployed vascular access port over the delivery configuration. This also improves fixation of the port after deployment. All three of these delivery to deployment changes, surface area to volume ratio reduction, volume increase, and base area increase, can be provided independently or in any combination of two or more in any given embodiment. Some advantageous embodiments, such as those shown in FIGS. 5, 7, and 8, implement all three of these changes.

Another advantageous feature of some embodiments described herein is that the transition from delivery configuration to deployed configuration may be accomplished with a linear sliding motion along the implantation incision to the implantation site/void. Preferably, only the linear sliding motion is required. No threads requiring a rotating motion, no fasteners, no separate catheter or tool access procedures are required in order to engage the components of the vascular access port in accordance with the principles described herein.

Furthermore, in some embodiments, the port body extension is implanted first. This component may be a rigid, semi-rigid or flexible polymer (e.g., silicone or a monolithic plastic, for example) or metal part with no fluid delivery functionality. This component can be easier to install without having to evaluate orientation issues relating to functionality. Once the extension is implanted, the port body with the septum can be slid down the same incision to engage the already correctly implanted extension.

Reference is now made to FIGS. 3A-3D, which schematically illustrate respectively side cross-sectional view and top views of exemplary subcutaneously formable vascular access port 30. Port 30 may be a variation of port 20 and may be configured same or similar in function and/or structure to either one of ports 10 and 20, and/or deployed similarly thereto, with or without catheter 15.

Figure 3A:
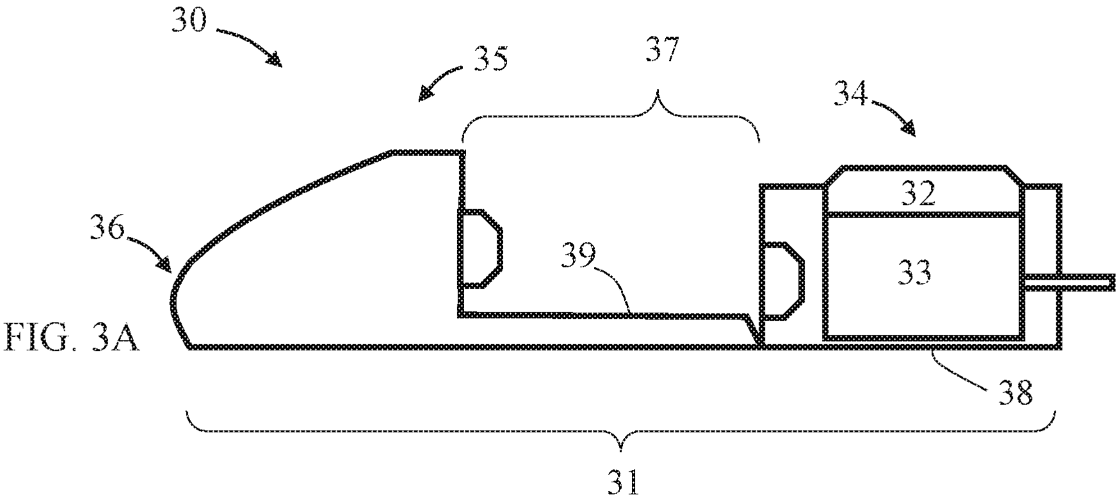
FIGS. 3A-3D schematically illustrate respectively side cross-sectional view and top views of another exemplary subcutaneously formable vascular access port, comprising a first port body member connectable to a second port body member, in accordance with some embodiments.
Figure 3B:
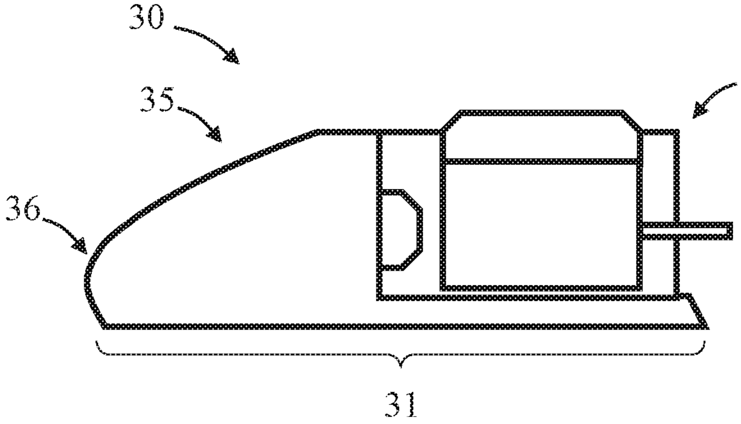
Figure 3C:
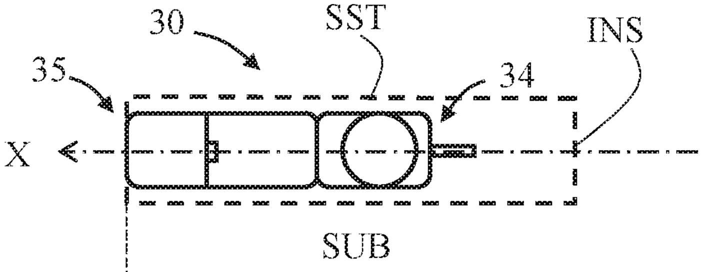
Figure 3D:
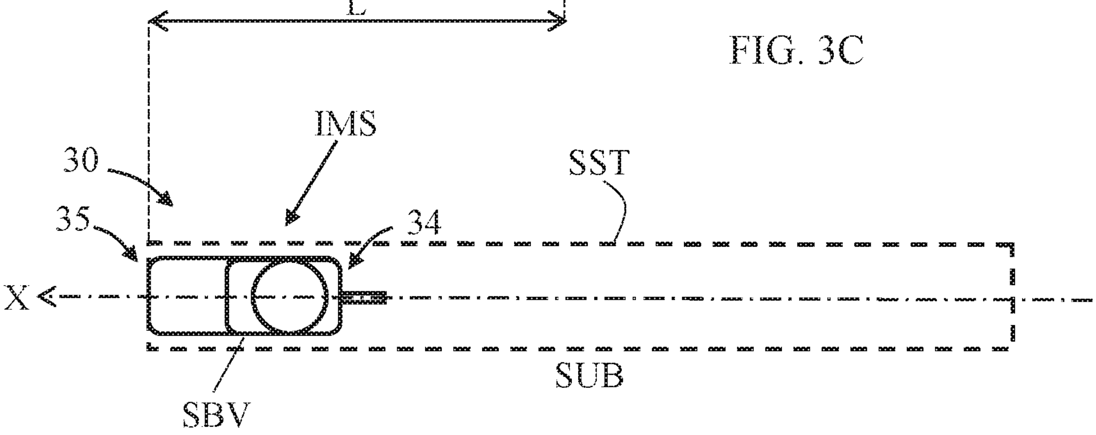

Port 30 includes a port body 31 coupled with a septum member 32 covering a cavity 33 defined by port body 31. Port body 31 is provided in a delivery configuration (shown in FIGS. 3A and 3C), having an elongated form extending along longitudinal axis X, and is selectively changeable to a deployed configuration (as shown in FIGS. 3B and 3D) by changing in size parallel to longitudinal axis X.

Port body 31 includes a first port body member 34 and a second port body member 35 interconnectable with each other and provided at least partially separated with each other when in the delivery configuration. Second port body member 35 stabilizes first port body member 34 when port body 31 is in the deployed configuration, and optionally has a maximal cross-sectional area of greater than a maximal cross-sectional area of first port body member 34.

First port body member 34 entirely defines cavity 33 and is directly connected to septum member 32. Second port body member 35 includes an edge 36 pointing away from first port body member 34, relative to the longitudinal axis X, configured for affecting atraumatic tissue layers separation when forced to pass in-between tissue layers, such as in the increase in length L of subcutaneous surgical tunnel SSL from a first position of port 30 shown in FIG. 3C to a second position shown in FIG. 3D.

Port body 31 is configured to affect joining of first port body member 34 with second port body member 35 when changing to the deployed configuration. When connected, first port body member 34 sits with a bottom portion 38 thereof on a top portion 39 of second port body member 35, such that the second port body member 35 functions as a base structure of port body 31 when in the deployed configuration.

For changing into the deployed configuration, first port body member 34 is subjected to move towards second port body member 35 along longitudinal axis X, thereby diminishing a gap 37 formed between respective boundaries of first and second port body members 34 and 35, then to engage respective portions of first and second port body members 34 and 35, and optionally to affect interlocking of first port body member 34 with second port body member 35. Gap 37 may be filled with a compressible substance such as a fluid, a flexible material or a viscoelastic material. Motion of first port body member 34 relative to second port body member 35 may be restricted to a predefined path relative longitudinal axis X.

For deploying vascular access port 30 in a body of a subject (e.g., subject SUB), an incision INS is made in proximity to a target implantation site (e.g., implantation site IMS) in the subject body. A subcutaneous void SBV may be formed between or beneath skin tissue layers (e.g., skin tissue layers SKL) at target implantation site IMS. Vascular access port 30 is inserted into the subcutaneous void SBV when port body 31 is provided in the delivery configuration (FIG. 3C). Each of first and second port body members 34 and 35 are passed, either together or one after the other, to the target implantation site IMS. Vascular access port 30 is then deployed by changing port body 31 into the deployed configuration by joining first port body member 34 with second port body member 35, thereby diminishing gap 37 and decreasing size of port body 31 along longitudinal axis X (FIG. 3D). The subcutaneous void SBV may be initially formed, or increased in size, as a result of inserting port 30 by forcing port body 31, optionally particularly second port body member 35, within the subject body through incision INS.

As part of port 30 deployment, or as a distinct step, catheter 15 is provided and implanted for providing fluid communication between cavity 33 and vasculature VSC of subject SUB (similarly to as shown in FIGS. 1A and 1B and as described above).

Optionally, a subcutaneous surgical tunnel SST is created between incision INS and target implantation site IMS, and port 30 is delivered through the surgical tunnel SST to the subcutaneous void SBV. Optionally, port 30 and parts thereof are delivered through a lumen of an elongated delivery device, optionally in a form of a surgical tunneler, extending along surgical tunnel SST. The elongated delivery device may include a rail and configured to restrict motion of first and/or second port body members 34 and 35 to travelling along the rail.

Optionally and alternatively, incision INS is located at the surface of, and serves as opening directly into, implantation site IMS, without having a surgical tunnel extending and connecting therebetween. In some such embodiments, first catheter end 17 is inserted into the subject body via a second incision IN2 remote to incision INS (as shown in FIG. 1B), and subcutaneous surgical tunnel SST is created between second incision IN2 and incision INS. Optionally, second catheter end 18 is delivered through the surgical tunnel SST towards from second incision IN2 to incision INS if for connecting with port 30 already present in subcutaneous void SBV, or already connected with port 30, optionally particularly to first port body member 34, and delivered together therewith to implantation site IMS.

Figure 4A:
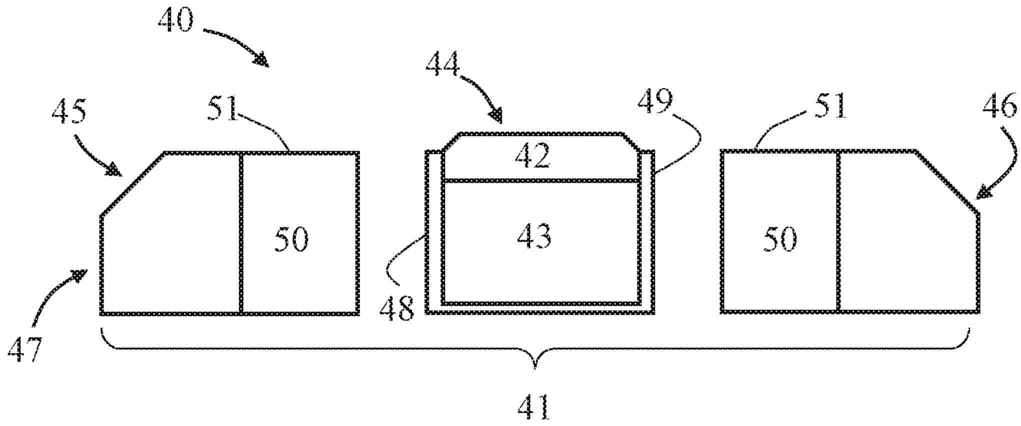
FIGS. 4A-4D schematically illustrate respectively side cross-sectional view and top views of another exemplary subcutaneously formable vascular access port, comprising a first port body member connectable to a second port body member and to a third port body member, in accordance with some embodiments.
Figure 4B:
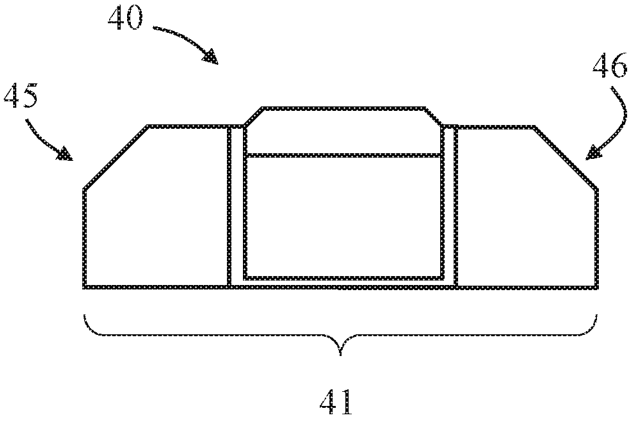
Figure 4C:
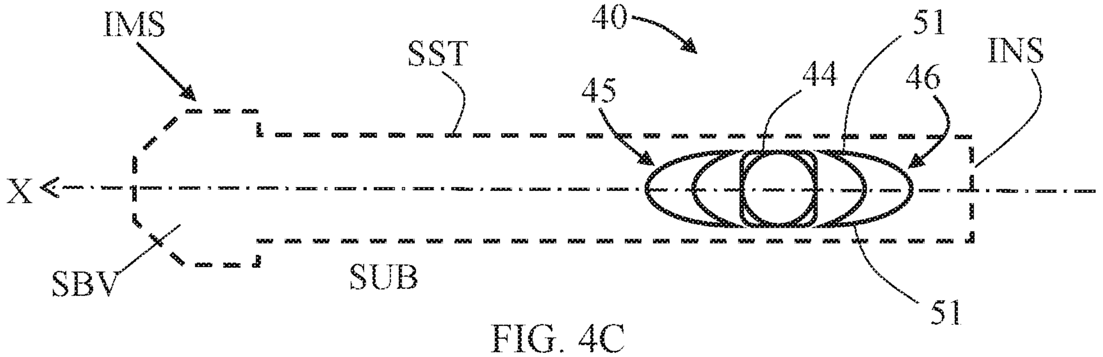
Figure 4D:
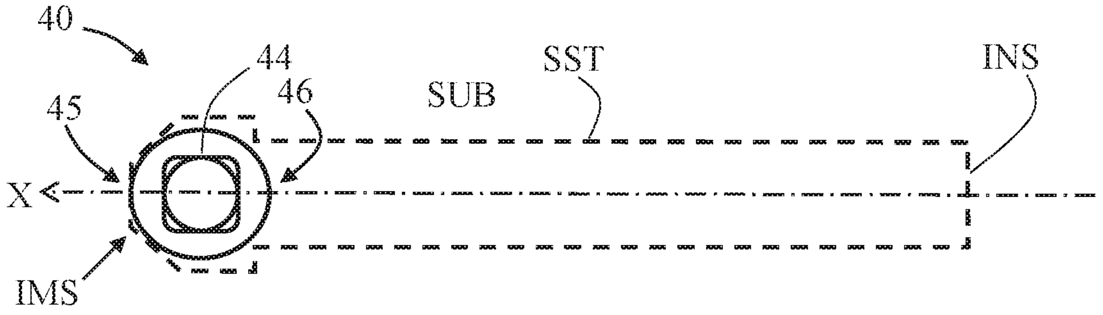

FIGS. 4A-4D schematically illustrate respectively side cross-sectional view and top views of another exemplary subcutaneously formable vascular access port 40. Port 40 may be a variation of port 20 and may be configured same or similar in function and/or structure to either one of ports 10, 20 and 30, and/or deployed similarly thereto, with or without catheter 15. Port 40 includes a port body 41 coupled with a septum member 42 covering a cavity 43 defined by port body 41. Port body 41 is provided in a delivery configuration (shown in FIGS. 4A and 40), having an elongated form extending along longitudinal axis X, and is selectively changeable to a deployed configuration (as shown in FIGS. 4B and 4D) by changing in size parallel to longitudinal axis X.

Port body 41 includes a first port body member 44, a second port body member 45 and a third port body member 46 interconnectable with each other and provided at least partially separated with each other when in the delivery configuration. Second and/or third port body member 45 and/or 46 stabilizes first port body member 44 when port body 41 is in the deployed configuration, and optionally has a maximal cross-sectional area of greater than a maximal cross-sectional area of first port body member 44.

First port body member 44 entirely defines cavity 43 and is directly connected to septum member 42. Second port body member 45 includes an edge 47 pointing away from first port body member 44, relative to the longitudinal axis X, configured for affecting atraumatic tissue layers separation when forced to pass in-between tissue layers. Port body 41 is configured to affect joining of first port body member 34 with each one of, and in-between, second port body member 45 and third port body member 46 when changing to the deployed configuration. When connected, first port body member 44 is connected with a front or distal side 48 to and against second port body member 45, and with a rear or proximal side 49 thereof to and against third port body member 46. Each of second and third port body members 45 and 46 has flexible portions 51 spaced with each other and pointing towards first body part member when in the delivery configuration. In the deployed configuration, flexible portions 51 are configured to expanded laterally and/or the embrace or encircle together first port body member 44, as shown in FIG. 4D. First port body member 44 is optionally substantially rigid thereby affecting reforming of flexible portions 51 when they are pressed against it to form port body 41 in its deployed configuration.

For changing into the deployed configuration, third port body member 46 is to be subjected to move towards first port body member 44, and the latter (or both) is subjected to move towards second port body member 45, along longitudinal axis X, thereby diminishing gaps 50 formed respectively between respective boundaries of first and second port body members 44 and 45 and between first and third port body members 44 and 46, also with respective flexible portions 51. Then respective portions of first, second and third port body members 44, 45 and 46 are subjected to engage, and optionally to affect interlocking of first port body member 44 with second port body member 45 and with third port body member 46. Gaps 50 may be formed or at least partly filled with a compressible substance such as a fluid, a flexible material or a viscoelastic material. Relative motions between first, second and third port body members 44, 45 and 46 may be restricted to a predefined path relative longitudinal axis X.

For deploying vascular access port 40 in a body of a subject (e.g., subject SUB), an incision INS is made in proximity to a target implantation site (e.g., implantation site IMS) in the subject body. A subcutaneous void SBV is formed between or beneath skin tissue layers (e.g., skin tissue layers SKL) at target implantation site IMS. Vascular access port 40 is inserted into the subcutaneous void SBV when port body 41 is provided in the delivery configuration (FIG. 40). Each of first, second and third port body members 44, 45 and 46 are passed, either together or one after the other, to the target implantation site IMS, Vascular access port 40 is then deployed by changing port body 41 into the deployed configuration by joining first port body member 44 with second and third port body members 45 and 46, thereby diminishing gaps 50 and decreasing size of port body 41 along longitudinal axis X (FIG. 4D). The subcutaneous void SBV may be initially formed, or increased in size, as a result of inserting port 40 by forcing port body 41, optionally particularly second port body member 45, within the subject body through incision INS.

As part of port 40 deployment, or as a distinct step, catheter 15 is provided and implanted for providing fluid communication between cavity 43 and vasculature VSC of subject SUB (similarly to as shown in FIGS. 1A and 1B and as described above).

Optionally, a subcutaneous surgical tunnel SST is created between incision INS and target implantation site IMS, and port 40 is delivered through the surgical tunnel SST to the subcutaneous void SBV. Optionally, port 40 and parts thereof are delivered through a lumen of an elongated delivery device, optionally in a form of a surgical tunneler, extending along surgical tunnel SST. The elongated delivery device may include a rail and configured to restrict motion of first, second and/or third port body members 44, 45 and 46 to travelling along the rail.

Optionally and alternatively, incision INS is located at the surface of, and serves as opening directly into, implantation site IMS, without having a surgical tunnel extending and connecting therebetween. In some such embodiments, first catheter end 17 is inserted into the subject body via a second incision IN2 remote to incision INS (as shown in FIG. 1B), and subcutaneous surgical tunnel SST is created between second incision 1N2 and incision INS. Optionally, second catheter end 18 is delivered through the surgical tunnel SST towards from second incision IN2 to incision INS if for connecting with port 40 already present in subcutaneous void SBV, or already connected with port 40, optionally particularly to first port body member 44, and delivered together therewith to implantation site IMS.

Figure 5A:
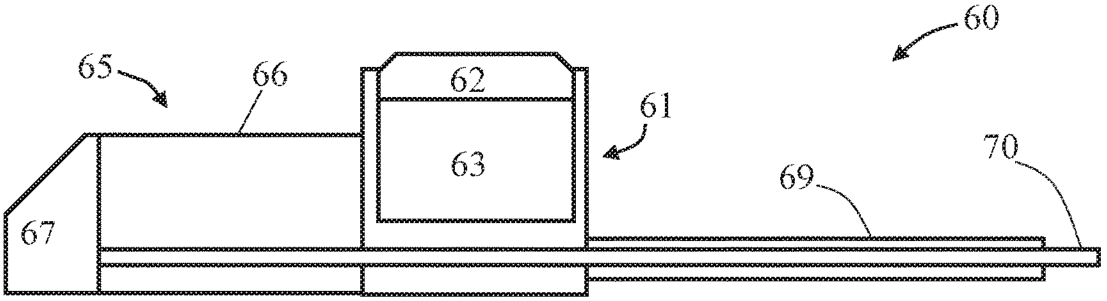
FIGS. 5A-5C schematically illustrate respectively side cross-sectional view and top views of another exemplary subcutaneously formable vascular access port, comprising a first port body member connectable to a laterally expandable second port body member, in accordance with some embodiments.
Figure 5B:
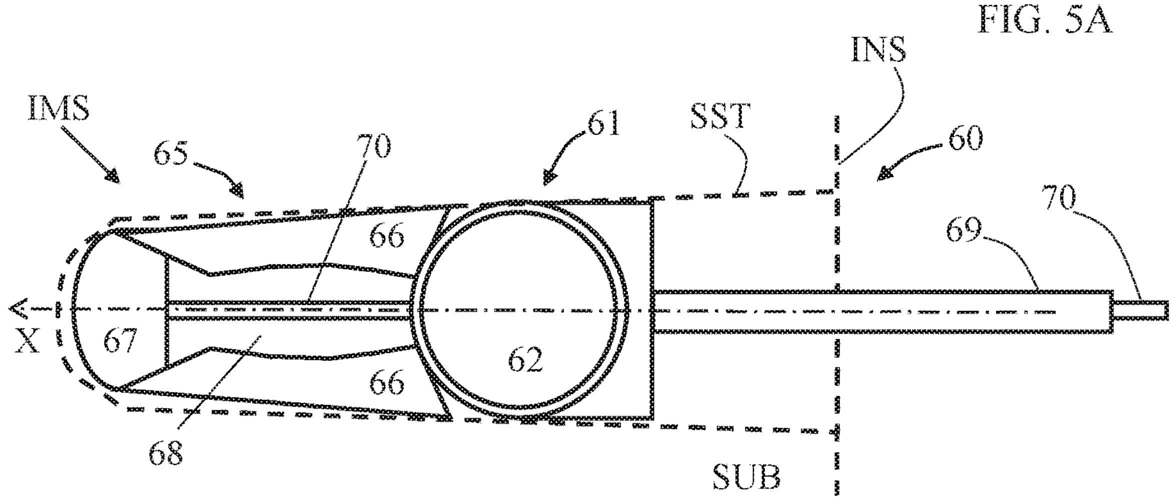
Figure 5C:
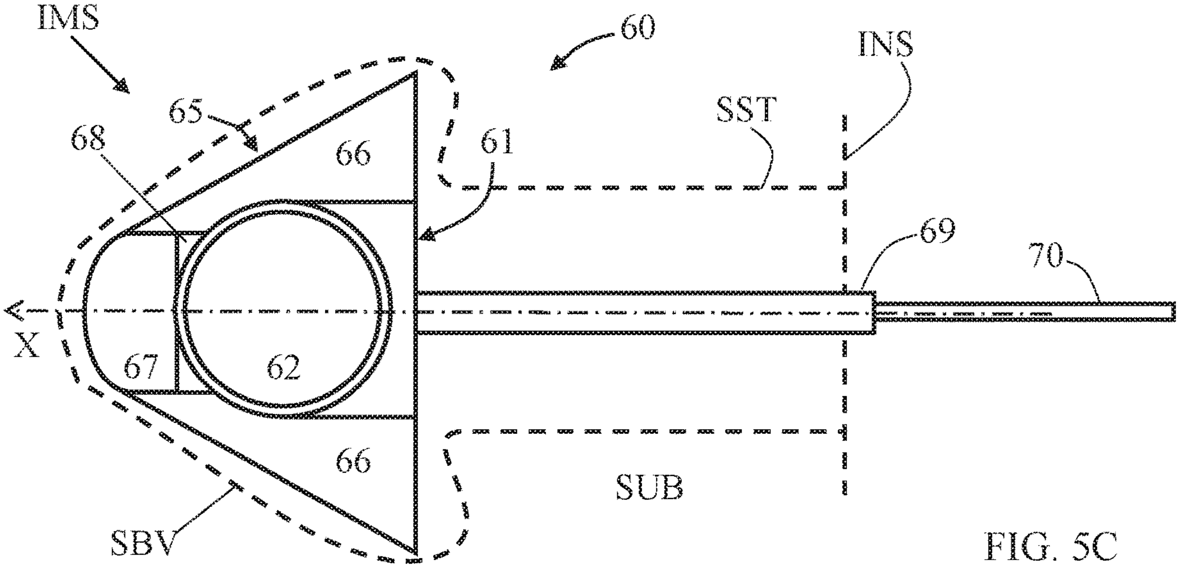

FIGS. 5A-5C schematically illustrate respectively side cross-sectional view and top views of another exemplary subcutaneously formable vascular access port 60. Port 60 may be a variation of port 20 and may be configured same or similar in function and/or structure to either one of ports 10, 20, 30 and 40, and/or deployed similarly thereto, with or without catheter 15. Port 60 includes a port body 61 that is coupled with a septum member 62 covering a cavity 63 entirely defined by port body 61. Port body 61 may also be referred to as a septum support 61. Cavity 63 has an inlet at its upper (posterior) portion thereof which is closed with septum member 62, and an outlet (fluidly connected to the inlet) in a lower (inferior) portion thereof in proximity to rear (proximal) end of port body 61 which is optionally opened to a connector (similar to connector 25 shown in FIG. 2A, for example) configured for providing fluid communication between the cavity and a lumen of a catheter or any other fluid delivery medium. Vascular access port 60 is provided in a delivery configuration (shown in FIGS. 5A and 5B), having an elongated form extending along longitudinal axis X, and is selectively changeable to a deployed configuration (as shown in FIG. 5C) by changing in size parallel to longitudinal axis X.

Port 60 further includes a second port body member configured as a port body extension 65 connectable with port body 61 and the two members (port body 61 and port body extension 65) are provided disconnected and at least partially separated from each other when vascular access port 60 is in the delivery configuration. Port 60 is selectively changeable subcutaneously from the delivery configuration to a deployed configuration wherein port body 65 extension adjoins and is fixedly connected to port body 61 to form a unified structure of vascular access port 60, being greater in volume, width and/or length than port body 61, optionally by at least 10%, or by at least 15%, or by at least 30%, or by at least 50%, in volume. Port body extension 65 is configured to stabilize and/or fixate port body 61, when port 60 is in the deployed configuration, by forming a unified structure shaped and sized effectively for increasing support and stability of port 60, relative to shape and size of port body 61 before connecting with port body extension 65, when implanted in a subcutaneous void in a subject's body. Although is some embodiments port body 61 is functionable as a vascular access port, it may lack sufficient stability due to size and/or shape thereof within the subcutaneous void, and this way can be more prone to migrate or turn over if not properly fastened to the body. Furthermore, port body extension 65 is configured to expand when assembling with port body 21, such that the unified structure of port 60 as a whole enlarges within the subcutaneous void stretching it further or even causing further dissection of tissues in a manner that increases stability and/or fixation within the subcutaneous void, optionally without need for applying fastening or suturing of port 60 to surrounding tissue.

Port body 61 is configured to affect change in shape and/or size of port body extension 65 by engaging, joining and connecting to port body extension 65, when port 60 changes to the deployed configuration. As part of the changing process of vascular access port 60 from the delivery configuration to the deployed configuration, port body 61 is moved distally, optionally by force applied by the operator, towards port body extension 65 so as to diminish a gap formed between respective boundaries of port body 61 and port body extension 65 in the delivery configuration. When properly joined and pressed against each other, the two members fixedly connect by having port body 61 interlocking with port body extension 65.

Port body 61 is configured to deform port body extension 65 and force it to expand laterally, when vascular access port 60 changes to the deployed configuration. Port body extension 65 includes two flexible portions 66 extending backwardly (towards port body 61, in the delivery configuration) from a front edge 67. Port body extension 65, with flexible portions 66 thereof, enclose an inner surface shaped in accordance with outer surface of port body 61 such that, when port body 61 is pushed or pressed against the inner surface of port body extension 65, flexible portions 66 rotate outwardly (away from longitudinal axis X, respectively) about front edge 67, causing port body extension 65 to laterally expand, and eventually embrace outer surface of port body 61. Optionally, port body extension 65 is deformable under force applicable by port body 61 thereto when port body 61 is pushed against its inner surface, such that the inner surface conforms at least partially to a shape imposed by the outer surface of port body 61, whereas port body 61 is configured to maintain size and shape thereof when pressed against port body extension 65,The final shape of vascular access port 60 in its unified structure resembles a generally triangular shape (in top view), as shown in FIG. 5C, optionally a three sided polygon, a circular triangle, or an equilateral triangle, while port body 61 may resemble a non-triangular shape, as shown in FIG. 5B.

Front edge 67 is optionally configured for surgically forming a subcutaneous tunnel beneath skin layer of a live subject, and/or for forming a subcutaneous void for implanting vascular access port 60 therein. Edge 67 is optionally rounded or chamfered, pointing away from port body 61, relative to the longitudinal axis X, and is configured for affecting atraumatic tissue layers separation when forced to pass therebetween. Each of flexible portions 66 may also have a rounded or chamfered edge pointing laterally outwardly relative to longitudinal axis X, such that upon outward rotation they may affect stretching and/or further atraumatic tissue layers separation when forced against tissue layers forming walls of subcutaneous void housing port body extension 65, during change of vascular access port 60 to the deployed configuration. Relative (axial) motion between port body 61 and port body extension 65, and interlocking by pressing them against each other, is accomplished using shafts which can be manipulated at a remote proximal location depending on their length, optionally including a first shaft 69 that is connected with distal end thereof to port body 61, and a second shaft 70 that is connected with a distal end thereof to port body extension 65.

For changing into the deployed configuration, port body 61 moves towards port body extension 65 along longitudinal axis X thereby diminishing a gap 68, formed between respective boundaries of port body 61 and port body extension 65 and with respective flexible portions 66. Gap 68 may be at least partly covered and/or filled with a compressible substance, a fluid, a flexible material or a viscoelastic material. Relative motions between port body 61 and port body extension 65 may be restricted to a predefined path relative longitudinal axis X.

Port 60 can be configured for allowing or restricting to one or more operational maneuvers of shaft(s) 69 and/or 70, for example: facilitating/allowing manipulation of second shaft 70 to advance port body extension 65 until it reaches or exceeds the target implantation site (and optionally surgically forms or increases volume of the subcutaneous void), then optionally fixating second shaft 70 and/or port body extension 65 in place, then facilitating/allowing manipulation of first shaft 69 to advance port body 61 until it reaches and joins port body extension 65. Optionally and alternatively, vascular access port 60 is configured to allow more flexibility and the operator can optionally implement one of different schemes to manipulate shafts 69 and 70, separately and/or together.

For deploying vascular access port 60 in a body of a subject (e.g., subject SUB), an incision INS is made in proximity to a target implantation site (e.g., implantation site IMS) in the subject body. Optionally, a subcutaneous surgical tunnel SST is created between incision INS and target implantation site IMS, and port 60 is delivered through the surgical tunnel SST to the subcutaneous void SBV. The surgical tunnel length is optionally a few centimeters in length, optionally greater than 5 cm, for example. Optionally, port 60 and parts thereof (including port body 61 and port body extension 65) are delivered through a lumen of an elongated delivery device, optionally in a form of a surgical tunneler, extending along surgical tunnel SST. The elongated delivery device may include a rail and may be configured to restrict motion of port body 61 relative to port body extension 65 in a chosen direction therealong, such as to travelling along the rail.

A subcutaneous void SBV is formed between or beneath skin tissue layers (e.g., skin tissue layers SKL) at target implantation site IMS optionally using a dedicated device, the tunneler or the front end of port 60, for example. Vascular access port 60 is inserted into the subcutaneous void SBV when port body 61 is provided in the delivery configuration (FIG. 5B). First body extension 65 is first to enter subcutaneous void SBV, which is already present or formed with front edge 67. Delivery is performed when vascular access port 60 is in delivery configuration, so port body 61 and port body extension 65 are passed either together (while maintaining gap 68 therebetween) or one after the other, to the target implantation site IMS. Vascular access port 60 is then put into the deployed configuration. The subcutaneous void SBV is forced into a greater volume as a result of assembling port 60 and lateral expansion of port body extension 65 within subcutaneous void SBV. Increasing the volume of subcutaneous void SBV can result in compaction of tissue mass surrounding port body extension 65, thereby increasing fixation and/or stability of vascular access port body 60 in the target implantation site IMS.

As part of port 60 deployment, or as a distinct step, catheter 15 is provided and implanted for providing fluid communication between cavity 63 and vasculature USC of subject SUB (similarly to as shown in FIGS. 1A and 1B and as described above).

In some other embodiments, incision INS is located at the surface of, and serves as opening directly into, implantation site IMS, without having a surgical tunnel extending and connecting therebetween. In some such embodiments, first (distal) catheter end 17 is inserted into the subject body via a second incision IN2 remote to incision INS (as shown in FIG. 1B), and subcutaneous surgical tunnel SST is created between second incision IN2 and incision INS. Optionally, second (proximal) catheter end 18 is delivered through the surgical tunnel SST towards from second incision IN2 to incision INS if for connecting with port 60 already present in subcutaneous void SBV, or already connected with port 60, optionally particularly to first port body member 64, and delivered together therewith to implantation site IMS.

Figure 6A:
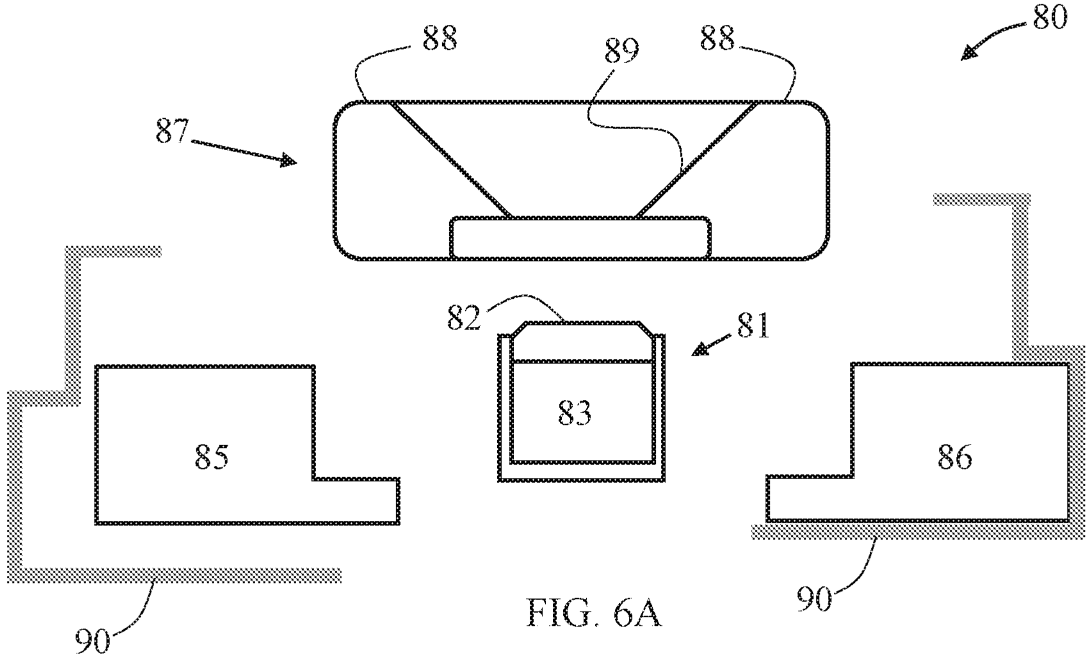
FIGS. 6A-6C schematically illustrate respectively side cross-sectional view and top views of another exemplary subcutaneously formable vascular access port, comprising a port body with an upper frame portion having a funnel shaped inner surface, in accordance with some embodiments.
Figure 6B:
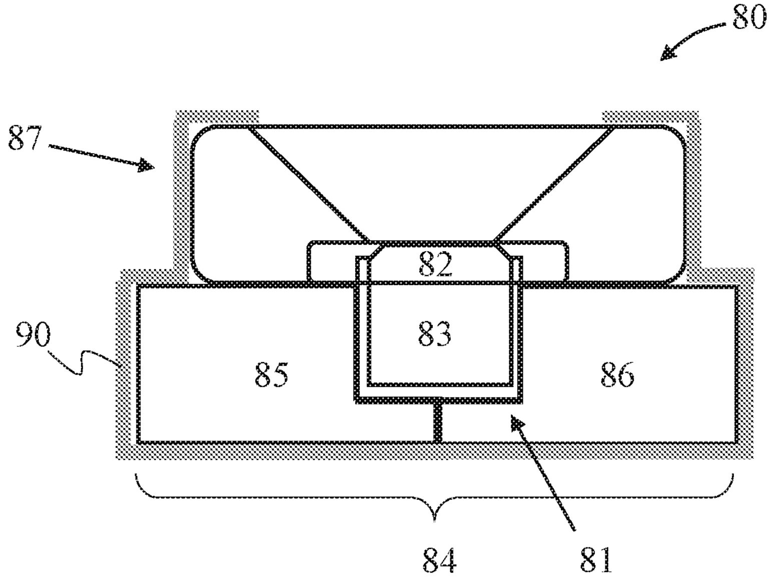
Figure 6C:
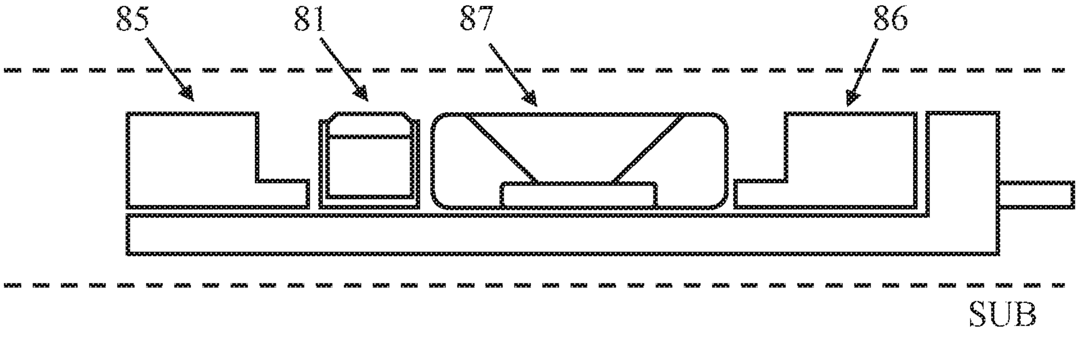

FIGS. 6A-6C schematically illustrate respectively side cross-sectional view and top views of another exemplary subcutaneously formable vascular access port 80. Port 80 may be a variation of port 20 and may be configured same or similar in function and/or structure to either one of ports 10, 20, 30, 40 and 60, and/or deployed similarly thereto, with or without catheter 15. Port 80 includes a first port body member 81 coupled with a needle activatable one-way valve or septum member 82 covering a cavity 83 defined by first port body member 81. First port body member 81 is provided as separated interlocking member that can be selectively joined with other interlocking members into a finalized assembly that forms port 80 in a deployed configuration.

Port 80 further includes a second port body member 84 that is formable with a plurality of interconnectable substructures including substructure 85 and substructure 86. When fully assembled and connected to first port body member 81, second port body member 84 functions as a supporting base, surrounds inferior periphery of first port body member 81, and configured to increase stability of port 80 so it will not unintentionally revolve or reposition after implantation, including during needle pricking through septum member 82.

The body of port 80 further includes an upper frame portion or member 87 that can be interlocked with first and/or second port body members 81 and 84, such that it is located over them and serves as intermediate channel between upper skin tissue and septum member 82. Upper member 87 includes a frame edge 88 that surrounds septum member 82 and protrudes upwardly relatively to a top surface thereof. Upper member 87 also includes a funnel shaped inner surface 89, enclosing a minimal diameter closest to septum member 82 and a maximal diameter adjacent to frame edge 89, for directing incoming needle tip towards septum member 82.

First and/or second port body members 81 and 84, and/or upper member 87, may be substantially rigid and configured to maintain size and shape thereof when pressed against each other. When deployed, port 80 may be covered with a flexible and/or cushioning material such as silicone rubber, in order to improve durability and safety for the patient during use, and/or for diminishing or preventing buildup of tissue ingrowth around and/or in-between the interlocked members building it. A cushion layer 90 may be attached, as a single member or distinct members, to some or all interlocking members building port 80, optionally to substructures 85 and 86 when in delivery configuration (as shown in FIG. 6A), and configured such that it encompasses portions of other interlocking members building port 80 when in deployed configuration (as shown in FIG. 6B).

For deploying vascular access port 80 in a body of a subject (e.g., subject SUB), an incision is made in proximity to a target implantation site (e.g., implantation site IMS) in the subject body. A subcutaneous void (e.g., subcutaneous void SBU) is formed between or beneath skin tissue layers (e.g., skin tissue layers SKL) at the target implantation site. First port body member 81, substructures 85 and 86 and upper member 87 are delivered separated, together or separately, to the target implantation site via the incision (as shown for example in FIG. 6C). Vascular access port 80 is then deployed by joining together all interlocking members as described above. As part of port 80 deployment, or as a distinct step, catheter 15 is provided and implanted for providing fluid communication between cavity 83 and subjects vasculature as described above.

Figure 7A:
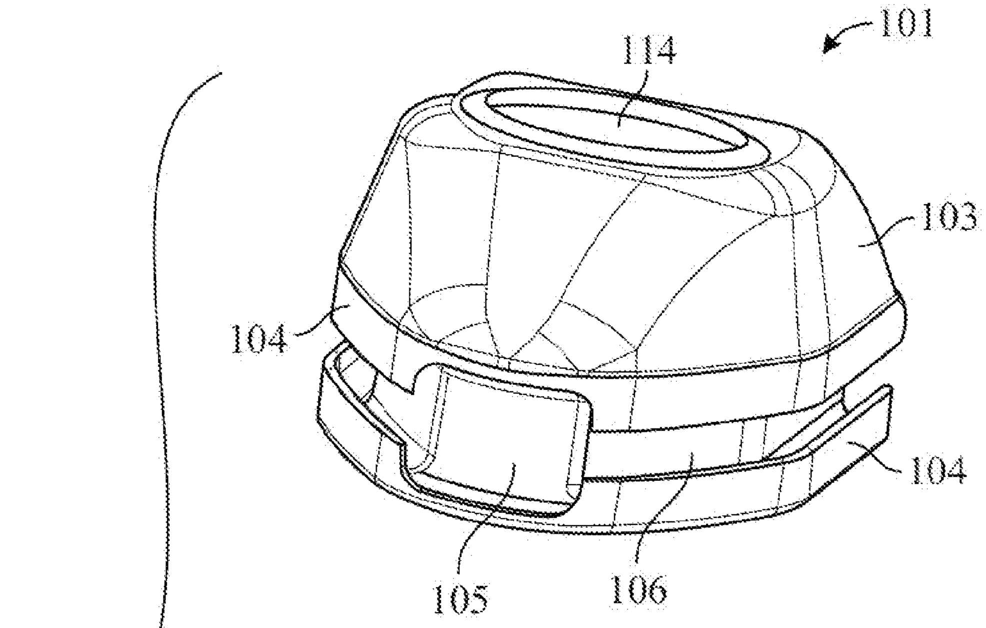
FIGS. 7A-7H schematically illustrate isometric views of a first exemplary implant comprising a first and a second members with interlocking edges, in accordance with some embodiments.
Figure 7B:
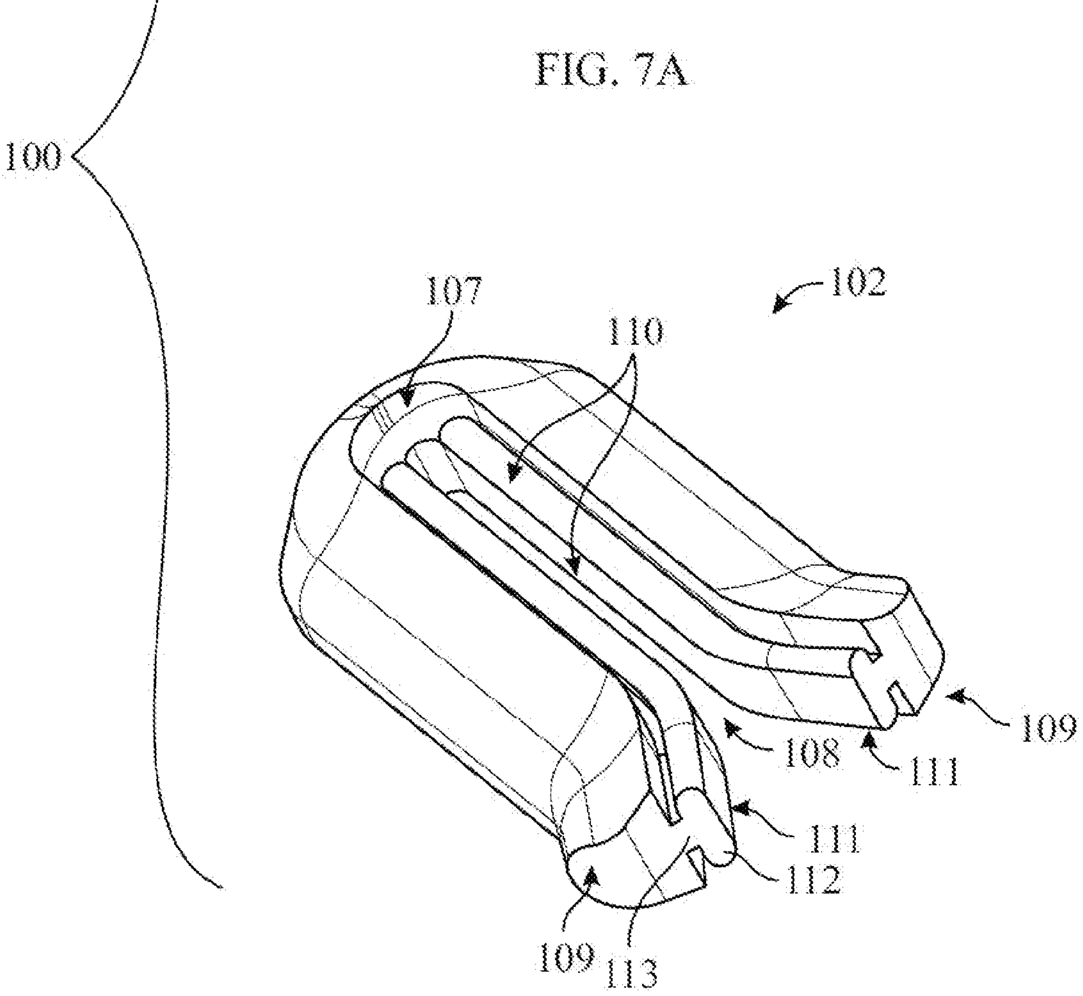
Figure 7C:
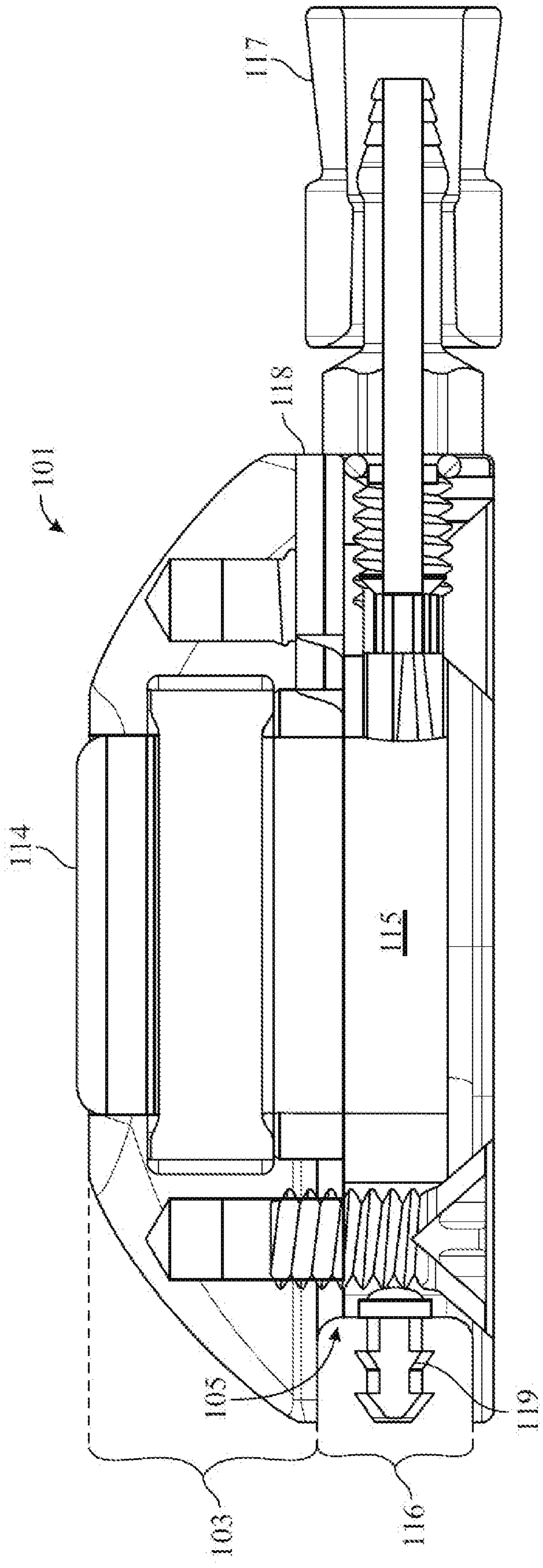
Figure 7D:
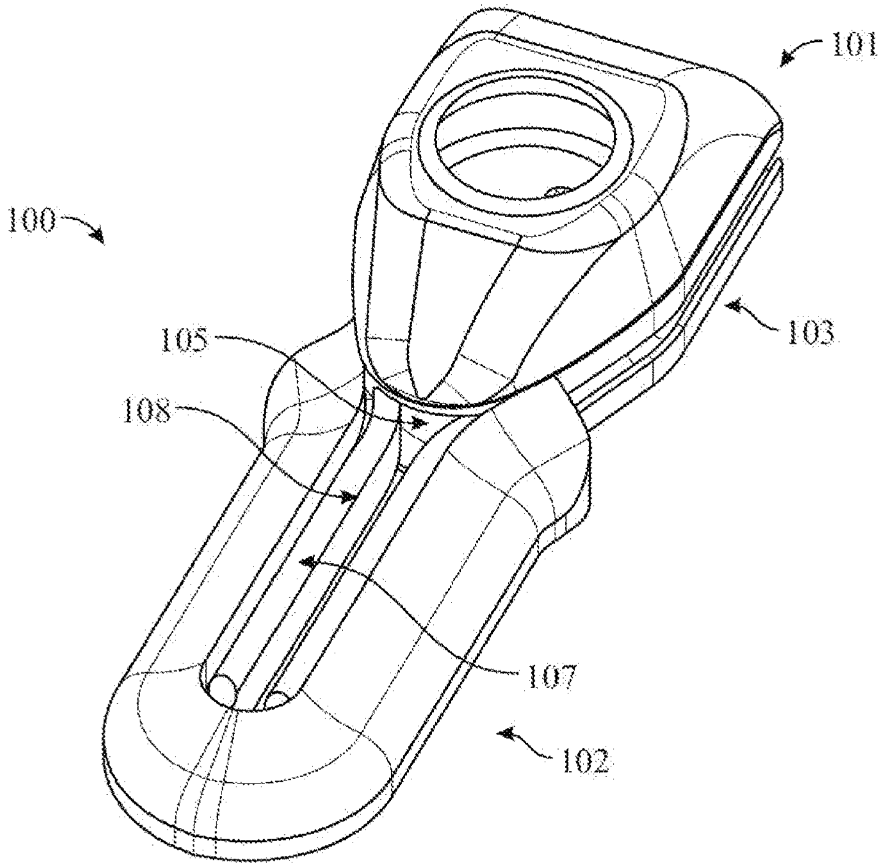
Figure 7E:
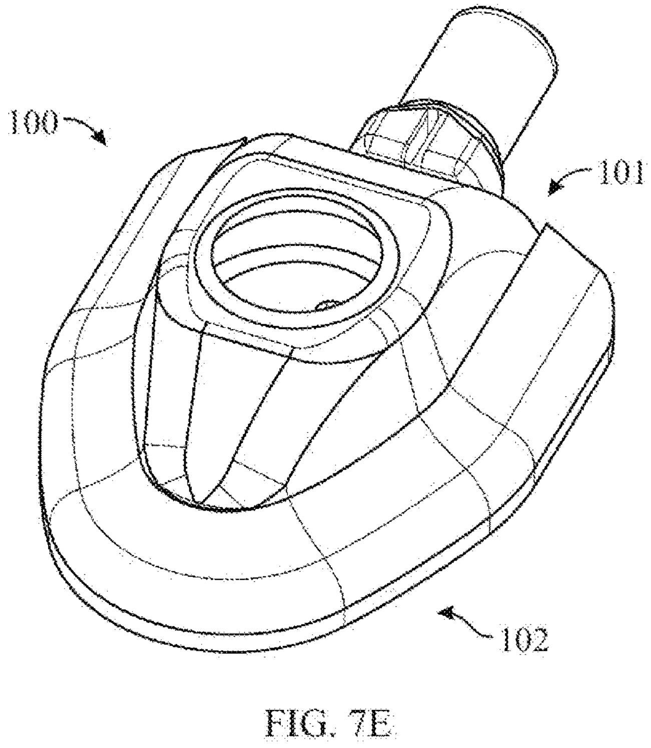

FIGS. 7A-7H schematically illustrate views of an implant 100, and components thereof. Implant 100 may be configured same or similar in function and/or structure to vascular access port 60 and/or to other ports such as 10, 20, 30, 40, or 80, and/or deployed similarly thereto, with or without catheter 15. Implant 100 includes a first member 101 (FIGS. 7A and 7C) configured as a port body (similar to port body 61) and a second member 102 (FIG. 7B) configured as a port body extension (similar to port body extension 65). First member 101 and second member 102 are interconnectable with each other (as shown in FIG. 7E) and, when implant 100 is in a delivery configuration, they are provided disconnected and at least partially separated with each other (as shown in FIG. 7D). First member (port body) 101 is functionally configured as a vascular access port and entirely defines a cavity 115 closed with a septum member 114, however connection thereof with second member (port body extension) 102 into a unified structure, as taught hereinafter, is suggested for providing a vascular access port in finalized (deployed) configuration that is advantageous in terms of stability and fixation to implantation site, relative to first member 101 alone.

FIG. 7C shows a cross-sectional view of first member (port body) 101. First member 101 has a posterior portion 103 and an inferior portion 116 enclosed with an external surface. Posterior portion 103 caps cavity 115 and includes an opening to the cavity that is blocked and sealed with septum member 114 connected to posterior portion 103. Inferior portion 116 includes front end 105, a rear end 118, and the base of the port body, and encloses most or all volume of cavity 115. Second member (port body extension) 102 includes an inner surface configured to engage and/or cover front end 105 and sides of inferior portion 116, when implant 100 (vascular access port) is in the deployed configuration. Port body inferior portion 116 comprises two opposing first member edges 104, one on each side thereof, with first member front end 105 located therebetween. Each one of the first member edges 104 has a longitudinally extending groove 106 made laterally inwardly towards centerline of first member 101. Second member 102 encloses an internal surface 107 that is accessible through a rear opening 108 provided on a second member rear 109. Internal surface 107 of second member 102 includes two opposing second member inner edges 110 each having a longitudinally extending ridge 111 projecting laterally therefrom towards centerline of second member 102.

First member 101 is configured to interlock longitudinally within second member 102 when pushed with front end 105 thereof through rear opening 108 and engaging external surface of the first member 101 with the internal surface 107 of second member 102 such that each one of ridges 111 interengages longitudinally with respective groove 106. Front end 105 is optionally equipped with an aligning member 119 projecting axially distally and configured to engage a mating recess in second member 102 thereby fixedly connecting, centering and/or aligning long axes of first and second members 101 and 102. By pushing first member 101 with front end 105 through the rear opening 108 and engaging external surface of first member 101 with internal surface 107, the internal surface 107 is forced to expand until it corresponds in shape and/or size to external surface of first member 101, and/or the second member 102 is forced to expand until the first member 101 interlocks with second member 102.

Each one of grooves 106 is aligned, and corresponding in cross-section, to the corresponding ridge 111; optionally but not necessarily all grooves and ridges are aligned. The cross-section shared by each corresponding pair of groove 106 and ridge 111 comprises a wider head section 112 and a narrow neck section 113. When the ridges 111 interengage longitudinally with grooves 106, head section 112 of each ridge cross section nests within the head section 112, and held in place by the neck section 113, of the respective groove cross section. As shown in FIG. 7D, implant 100 is in a fully assembled form when second member 102 surrounds front 105 and first member edges 104 and conforms to shape of external surface of first member 101, and particularly of port body inferior portion 116. In this configuration implant 100 has a final size and shape and is ready for deployment and use.

When in the deployed configuration, rear end 118 of first member 101 (particularly of port body inferior portion 116) is not covered with second member 102 (port body extension). The port body rear end 118 is connected or connectable via a connector 117 to a proximal end of a catheter for facilitating fluid communication between cavity 115 and a lumen of the catheter.

Figure 7F:
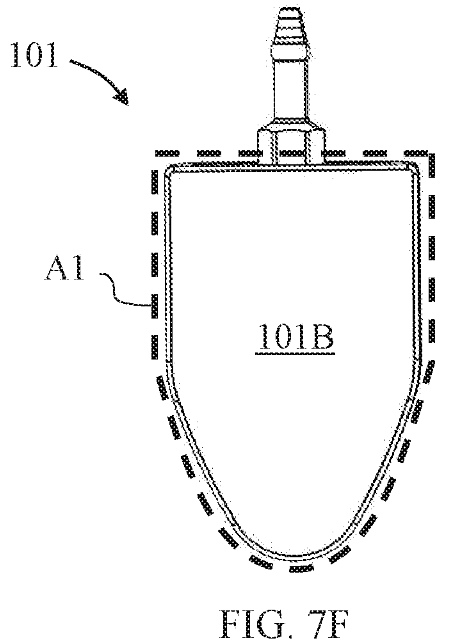
Figure 7G:
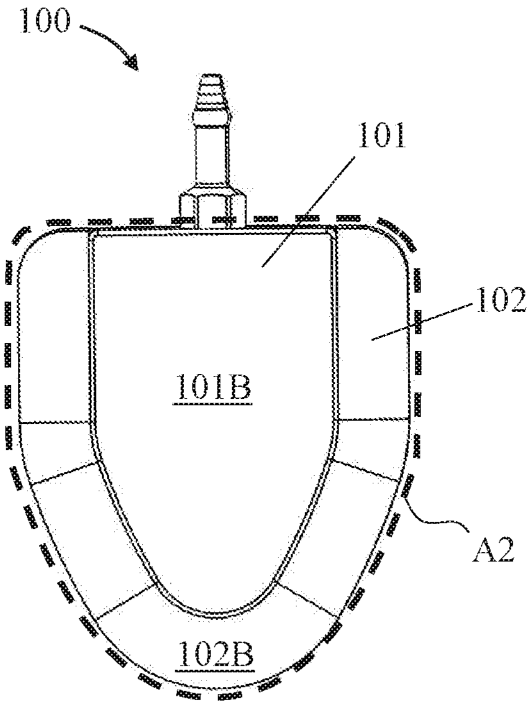
Figure 7H:
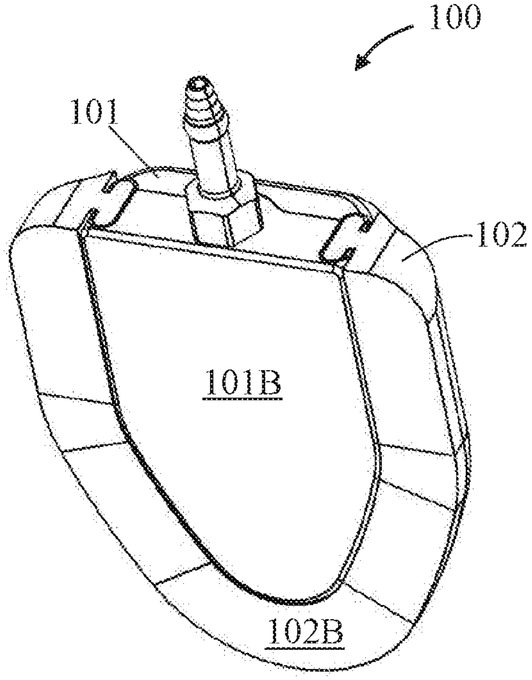

FIGS. 7F-7H show different views showing base (e.g., bottom or inferior) surfaces of first member (port body) 101 before and after assembling with second member (port body extension) 102 to form a unified structure of implant (vascular access port) 100. First member 101 has a first base surface 101B and second member 102 has a second base surface 102B. As shown in FIG. 7F, first base surface 101B has a first base area A1, and as shown in FIG. 7G, the unified implant 100 has a second base area A2 which is substantially greater than first base area A1. FIG. 7H shows that first base surface 101A and second base surface 102B are substantially flat and/or coincide with each other on same plane such that the unified structure of implant 100 has a substantially flat, level and/or even surface.

In some embodiments, second base area A2 is greater than first base area by at least 15%, optionally by at least 30%, optionally by at least 50%, optionally by at least 75%. In some such embodiments, first base area A1 is smaller than about 500 $mm^2$, optionally smaller than about 400 $mm^2$, optionally smaller than about 300 $mm^2$. Optionally, additionally or alternatively, second base area A2 is greater than about 300 $mm^2$, optionally greater than about 400 $mm^2$, optionally greater than about 500 $mm^2$. In an exemplary embodiment, first base area A1 is about 245 $mm^2$ and second base area A2 is about 465 $mm^2$, therefore second base area A2 is greater than first base area A1 by about 90%.

The total outer surface area of first member (port body) 101 encloses a first solid shape (shown in FIG. 7A, for example), and the total outer surface area of the unified implant 100, comprising the fully assembled first and second members 101 and 102, encloses a second solid shape (shown in FIG. 7E, for example). In some embodiments, the volume of the second solid shape (e.g., the volume of implant 100 in its unified structure) is greater than the volume of the first solid shape (e.g., the volume of first member 101 only) by at least 15%, optionally by at least 30%, optionally by at least 50%, optionally by at least 75%. In some such embodiments, the volume of the first solid shape is smaller than about 2,000 $mm^3$, optionally smaller than about 1,750 $mm^3$, optionally smaller than about 1,500 $mm^3$. Optionally, additionally or alternatively, the volume of the second solid shape is greater than about 2,000 $mm^3$, optionally greater than about 2,500 $mm^3$, optionally greater than about 3,000 $mm^3$. In an exemplary embodiment, the volume of the first solid shape is about 1,715 $mm^3$ and the volume of the second solid shape is about 2,715 $mm^3$, therefore the volume of the second solid shape is greater than the volume of the first solid shape by about 58%. Furthermore, the second solid shape (of the unified structure) has a lower surface area to volume ratio than the combined first member 101 (port body) and second member 102 (port body extension) when partially or wholly disengaged in the delivery configuration (as shown in FIG. 7D, for example), FIGS. 8A-8E schematically illustrate isometric views of an implant 120. Implant 120 may also be configured same or similar in function and/or structure to vascular access port 60 and/or to other ports such as 10, 20, 30, 40, or 80, and/or deployed similarly thereto, with or without catheter 15. Implant 120 includes a first member 121 (FIG. 8A) configured as a port body (similar to port body 61) and a second member 122 (FIG. 8B) configured as a port body extension (similar to port body extension 65). First member 101 and second member 102 are interconnectable with each other (as shown in FIG. 8E) and, when implant 100 is in a delivery configuration, they are provided disconnected and at least partially separated with each other (as shown in FIG. 8D). FIG. 8C shows first member 121 provided adjacent to part of second member 122, for illustrative purposes only. First member 121 is functionally configured as a vascular access port and entirely defines a cavity (similar to cavity 63 of port 60, for example) closed with a septum member (similar to septum 64 of port 60, for example), however connection thereof with second member 122 into a unified structure, as taught hereinafter, is suggested for providing a vascular access port in finalized (deployed) configuration that is advantageous in terms of stability and fixation to implantation site, relative to having first member 121 alone.

First member 121 is enclosed with an external surface 123 comprising a first member ridged edge 124 and a first member grooved edge 125 opposing the first member ridged edge 124, and a first member front 137 located therebetween. First member ridged edge 124 has a longitudinally extending first ridge 126, and first member grooved edge 125 has a longitudinally extending first groove 127.

Second member 122 encloses an internal surface 128 accessible through a rear opening 129 provided on a second member rear 130. Internal surface 128 includes a second member ridged (internal) edge 131 and a second member grooved (internal) edge 132 opposing the second member ridged side 131. Second member ridged edge 131 has a longitudinally extending second ridge 133, and second member grooved edge 132 has a longitudinally extending second groove 134. In a proper positioning (as shown in FIG. 8D), first groove 127 is aligned, and corresponding in cross-section, to first ridge 126, and second groove 134 is aligned, and corresponding in cross-section, to second ridge 133.

First member 121 is configured to interlock longitudinally within second member 122 when pushed with first member front 137 through rear opening 129 and engaging the external surface 123 of first member 121 with the internal surface 128 of the second member 122 such that first ridge 126 interengages longitudinally with second groove 134 and second ridge 133 interengages longitudinally with first groove 127. By pushing first member front 137 through rear opening 129 and engaging external surface 123 with internal surface 128, the internal surface 128 is forced to expand until corresponding in shape and/or size to external surface 123, and/or second member 122 is forced to expand until first member 121 interlocks with second member 122.

Figure 8B:
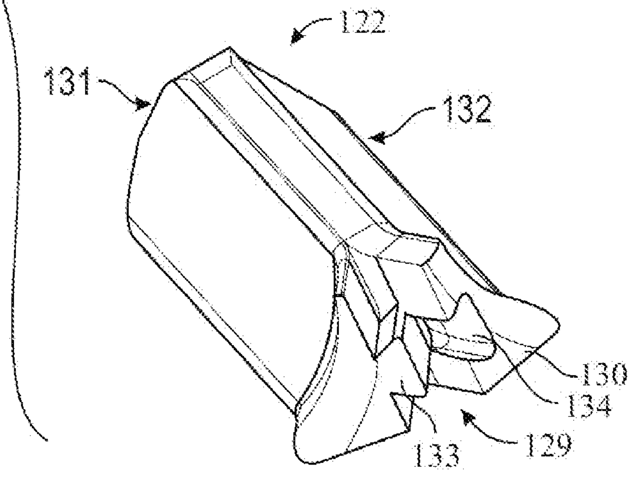
Figure 8C:
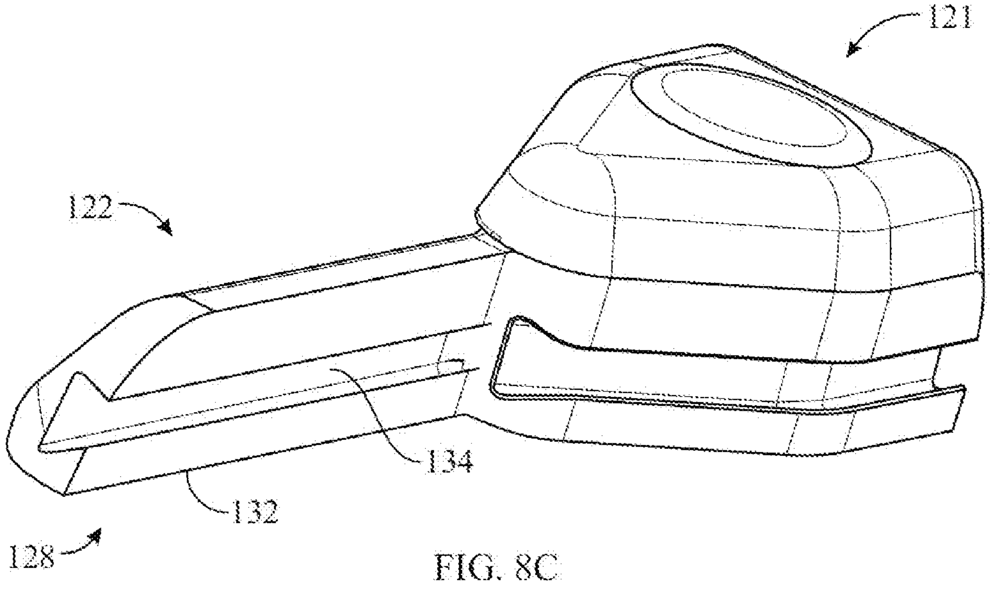
Figure 8D:
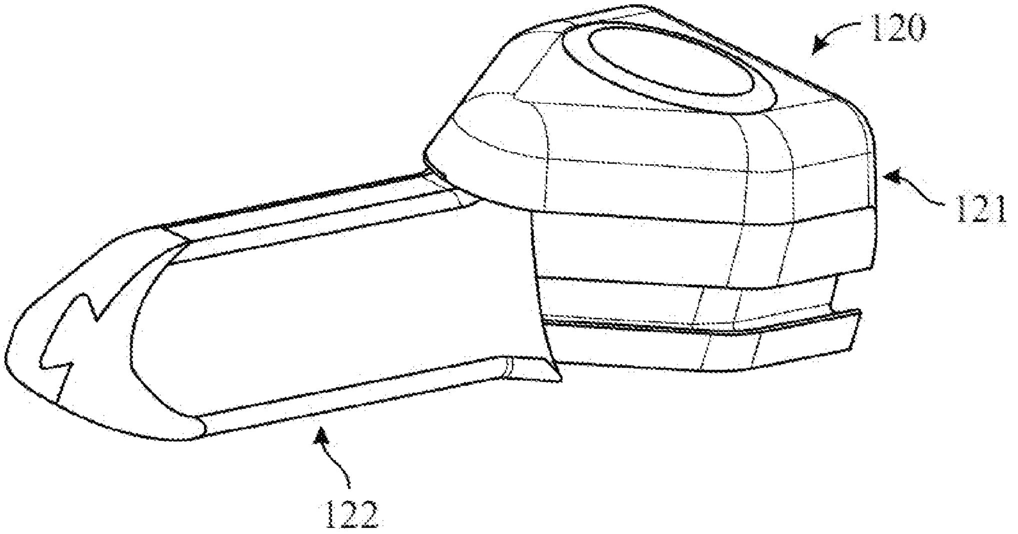
Figure 8E:
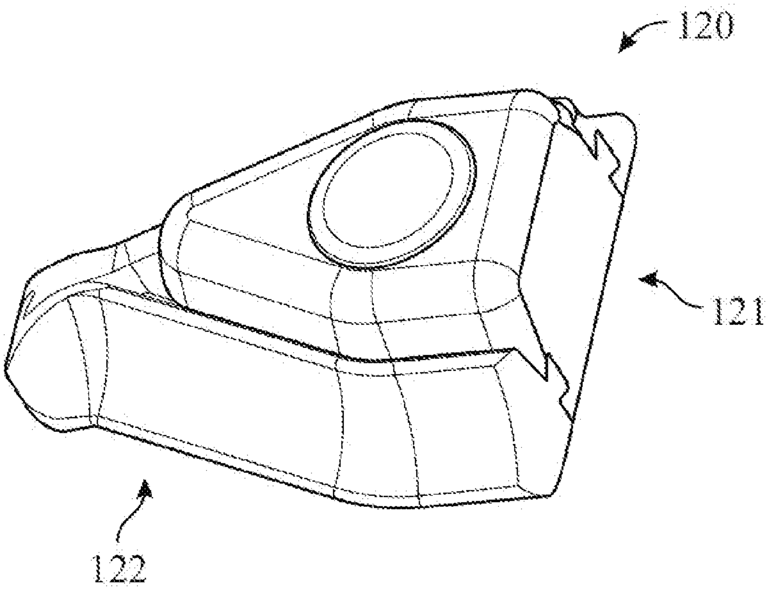

As shown in FIGS. 8B and 8D, second member 122 is provided with the internal surface 128 in a closed configuration, such that second ridge 133 interengages longitudinally and/or interlocks with second groove 134 in at least most of lengths thereof. By pushing first member front 137 through rear opening 129 and engaging external surface 123 with the internal surface 128, second ridge 133 is forced to disengage from second groove 134, optionally gradually in a direction from proximal end towards distal end thereof, optionally while engaging and/or interlocking with first groove 127 and first ridge 126, respectively.

First and second grooves, 127 and 134, and first and second ridges, 126 and 133, share a corresponding cross-section comprising a wider head section 135 and a narrow neck section 136. When first ridge 126 interengages longitudinally with second groove 134 and second ridge 133 interengages longitudinally with first groove 127, the head section 135 of the first and second ridges 126 and 133 cross section nests within the head section 135, and held in place by the neck section 136, of the respective first and second grooves 127 and 134 cross section. As shown in FIG. 8E, implant 120 is in a fully assembled form when second member 122 surrounds front 137 and first member edges 124 and 125 and conforms to shape of external surface 123. In this configuration implant 120 has a final size and shape and is ready for deployment and use.

FIGS. 9A-9H illustrate isometric views of an exemplary port delivery apparatus 150 and components thereof. Delivery apparatus 150 is configured for delivering a port body and a port body extension to a subcutaneous target location, held separated with each other, while optionally forming the target location and/or a surgical tunnel thereto. Delivery apparatus 150 is further configured to form a unified structure of a vascular access port by adjoining and assembling components thereof such as the port body and port body extension, and then to release the vascular access port in the target location, using controls equipped at a portion thereof that are manually operable remotely from outside patient's body.

Figure 9A:
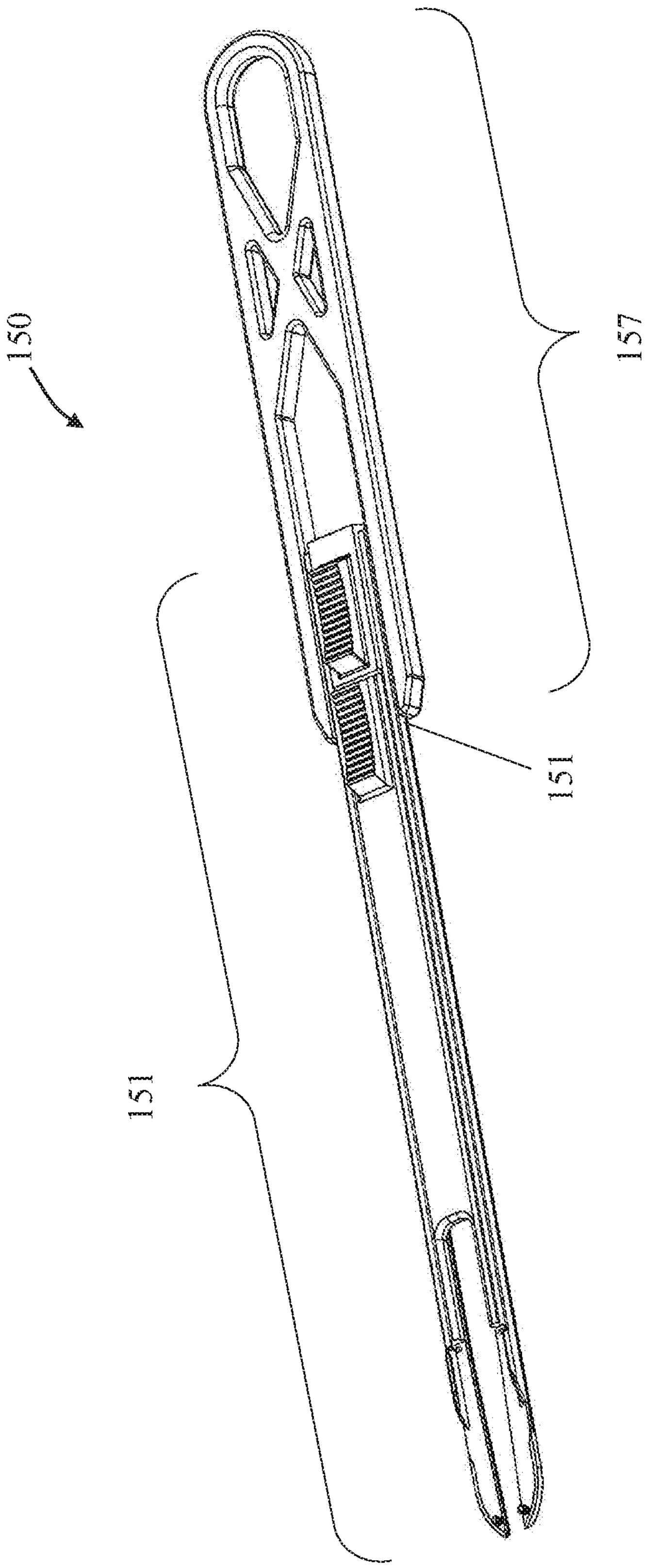
FIGS. 9A-9H schematically illustrate isometric views of an exemplary port delivery apparatus and components thereof, in accordance with some embodiments
Figure 9B:
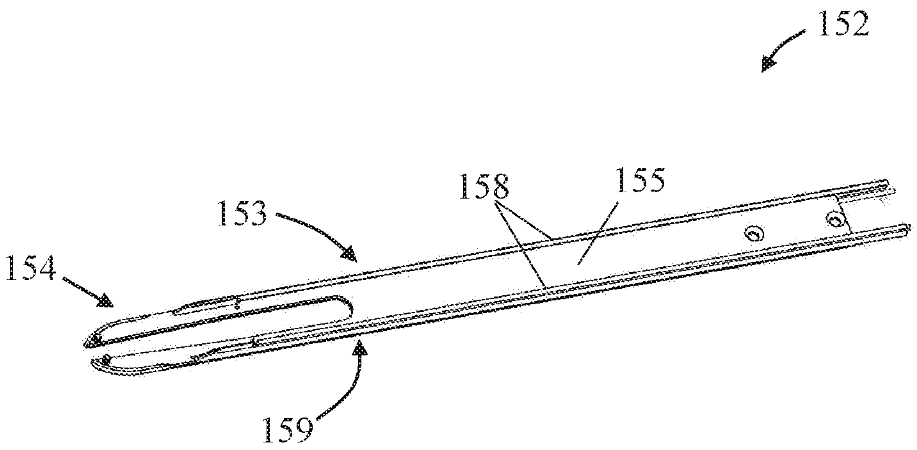
Figure 9C:
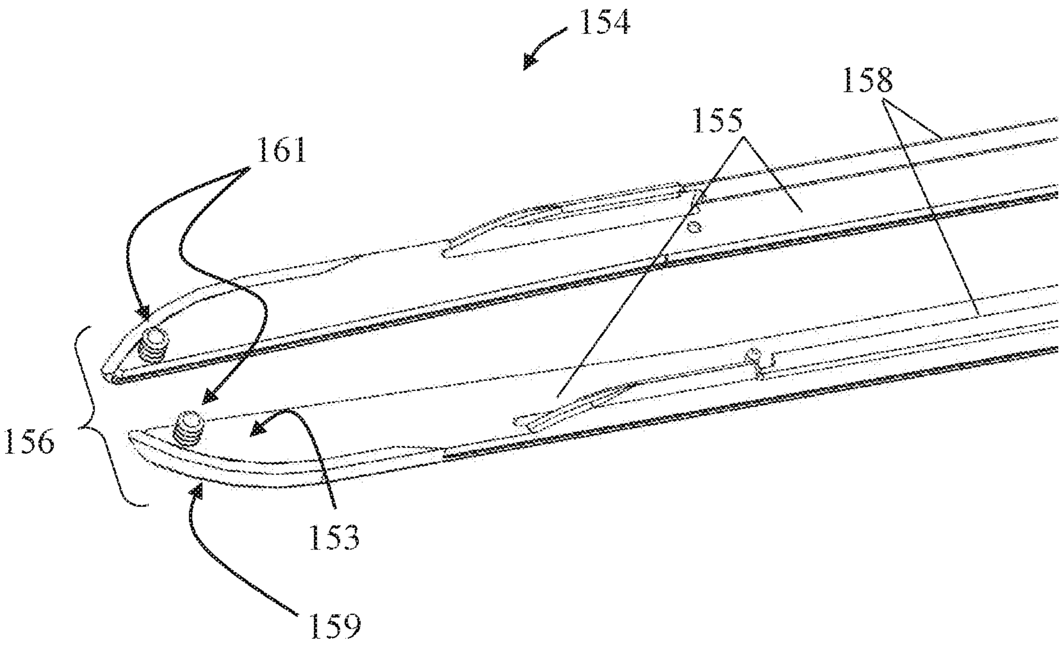

Port delivery apparatus 150 comprises an elongated delivery apparatus body 151 that includes a tissue penetrating front segment 152 (shown as a separate component in FIG. 9B, with a zoom-in view of its distal part in FIG, 9C). Front segment 152 is optionally at least 1 cm greater than length of the port body or of the vascular access port unified structure, and/or is optionally at least 4 cm, optionally at least 6 cm, in length. A handle 157 (shown as a separate component in FIG. 9F) is connected to a proximal portion of tissue penetrating front segment 152 for manual manipulation of front segment 152. Handle 157 may be aligned, as shown, and may be either fixedly or selectively pivotally, slidably and/or releasably connected to front segment 152.

Tissue penetrating front segment 152 ends with a dissection tip 156 configured for projecting distally relative to distal boundaries of the port body extension when attached to the delivery apparatus body 151. Dissection tip 156 is at least 1 mm, optionally at least 5 mm, in length, and it may be rounded along width and/or thickness thereof. Dissection tip 156 may be comprised of two or more distally extending generally elongated members, as shown, or be configured as a single element.

Figure 9D:
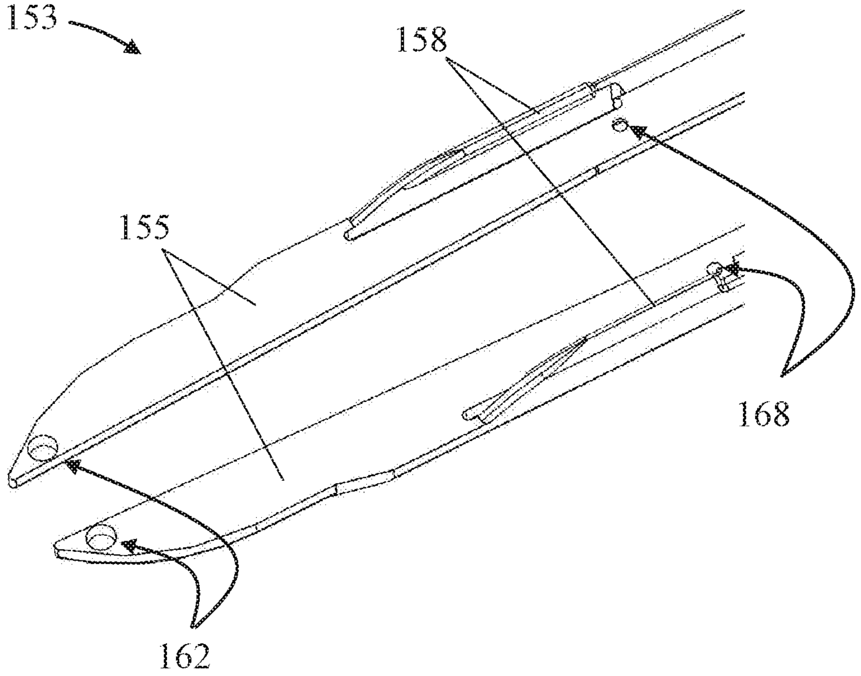

Front segment 152 includes a thin, flat support member 153 (shown, in distal/front part thereof, as a separate component in FIG. 9D) having a distal portion 154 configured for supporting the port body extension, and a sliding surface 155 configured for supporting and facilitating unhindered sliding of the port body thereon, towards the port body extension for example. A lateral barrier 158 is provided at each side of sliding surface 155, extending along some, most or all its length, configured to restrict direction of motion of the port body only to axial direction along sliding surface 155, by continuously engaging a portion of the port body and preventing motions thereof in directions other than the axial direction, during sliding of the port body along the sliding surface 155.

Figure 9E:
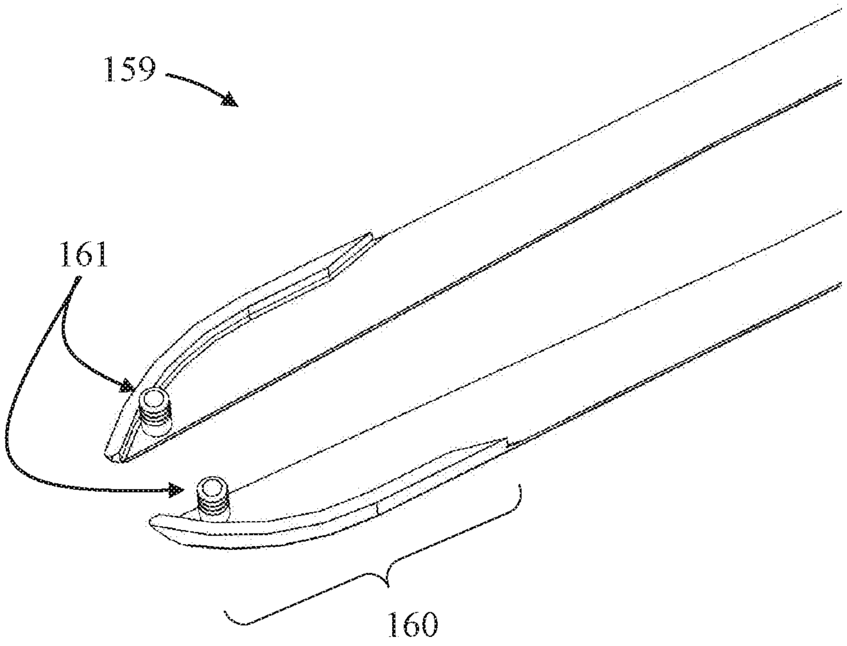
Figure 9F:
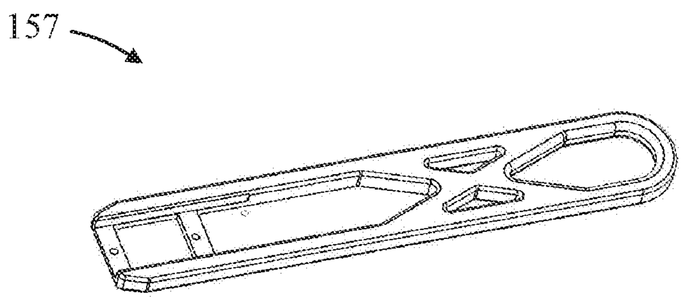
Figure 9G:
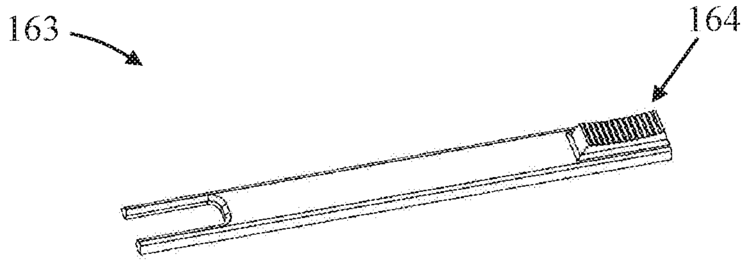
Figure 9H:
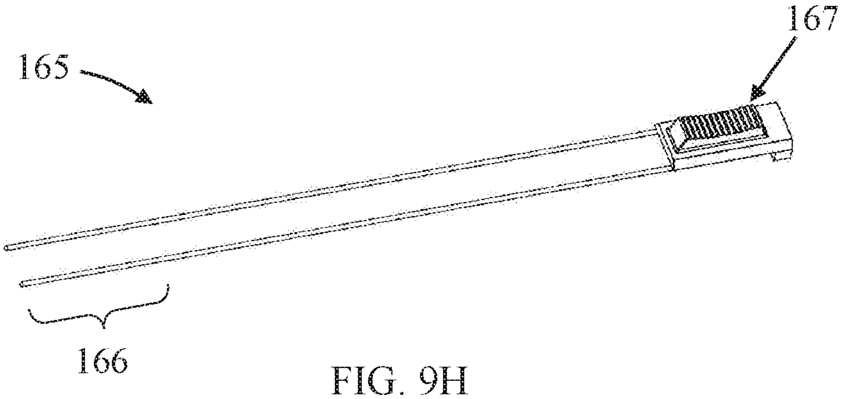

Tissue penetrating front segment 152 also includes a base member 159 (shown, in distal/front part thereof, as a separate component in FIG. 9E) configured for covering bottom surface of support member 153 which opposes sliding surface 155. Base member 159 includes a distal portion 160 covering the distal portion 154 of support member 153 and is coupled to prongs 161 protruding therefrom through openings 162 in distal portion 154 of support member 153. Prongs 161 are configured to engage mating recesses in a bottom portion of the port body extension for fixation to the port delivery apparatus.

Port delivery apparatus 150 includes a pusher 163 (shown as a separate component in FIG. 9G) slidably connected to delivery apparatus body 151 and selectively slidable along tissue penetrating front segment 152. Pusher 163 is configured to push the port body towards the port body extension for engaging and connecting therebetween to form the unified structure of the vascular access port. A first actuator 164 is provided at a proximal portion of pusher 163 in proximity to proximal end of tissue penetrating front segment 152 when the vascular access port is in the delivery configuration. Pusher 163 may include two or more prong-like members extending distally therefrom, as shown, for allowing room for a portion of a catheter for passing therethrough, or it may be configured as a single elongated member, for example.

Port delivery apparatus 150 also includes a releasing element 165 (shown as a separate component in FIG. 9H) slidably connected to delivery apparatus body 151 and selectively slidable along tissue penetrating front segment 152 within dedicated space(s) or track(s) provided between support member 153 and base member 159. Releasing element 165 is configured for separating distal portion 160 of base member 159 from contacting or close-proximity with the distal portion of support member 153, and this is achieved when a distal portion 166 of the releasing element 165 pushed into a narrower space or a crack therebetween. This causes prongs 161 to retract from the mating recesses in the port body extension, thus allowing release of the vascular access port from port delivery apparatus 150. A second actuator 167 is provided at a proximal portion of releasing element 165 and is provided in proximity to a proximal end of tissue penetrating front segment 152 when the vascular access port is in the delivery configuration. Releasing element 165 may include two or more prong-like members extending distally therefrom, as shown, or be configured as a single element, for example.

Figure 10:
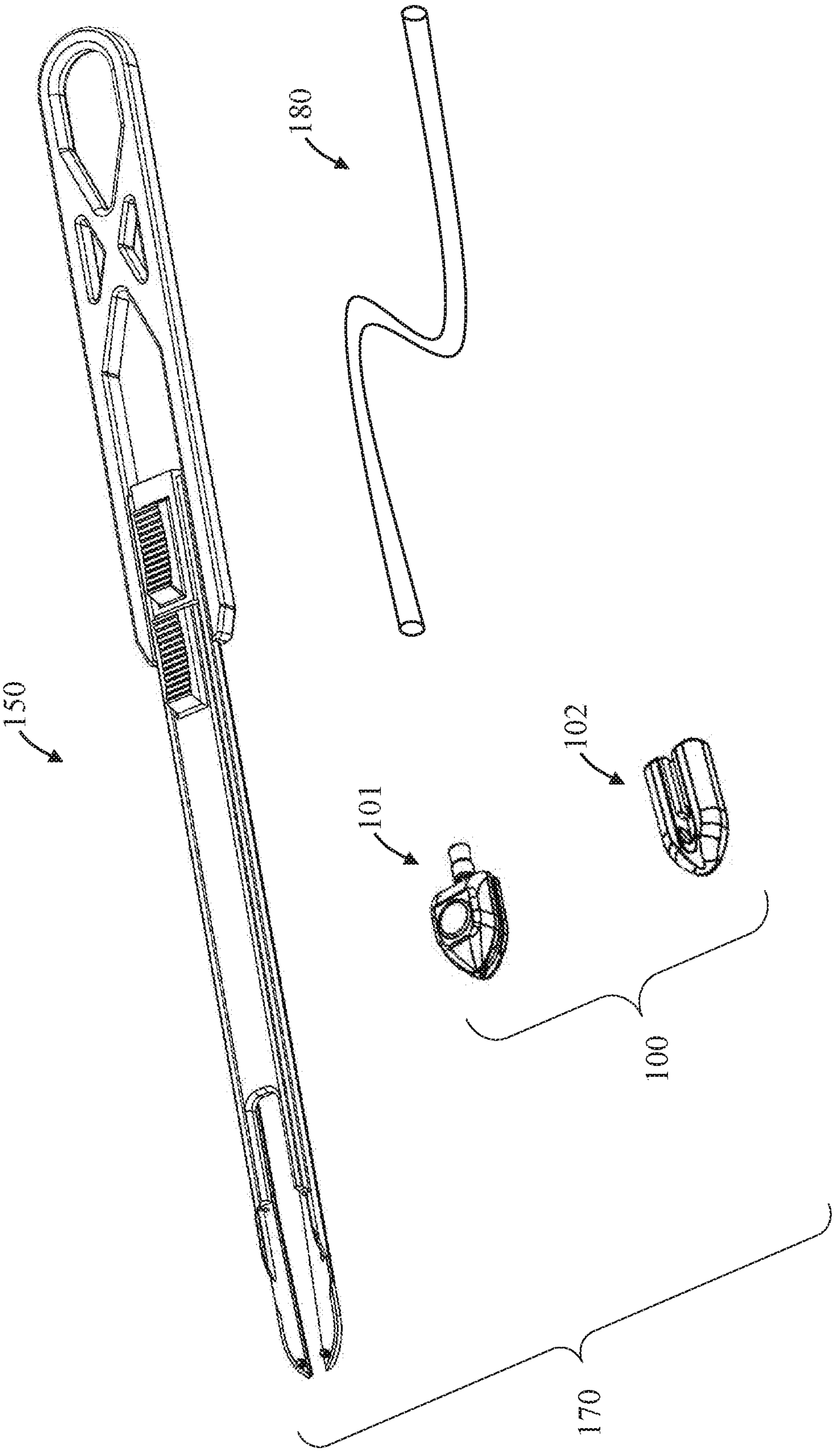
FIG. 10 illustrates an exemplary kit comprising at least components of the implant shown in FIGS. 7A-7E and the port delivery apparatus shown in FIGS. 9A-9H.
Figure 11A:
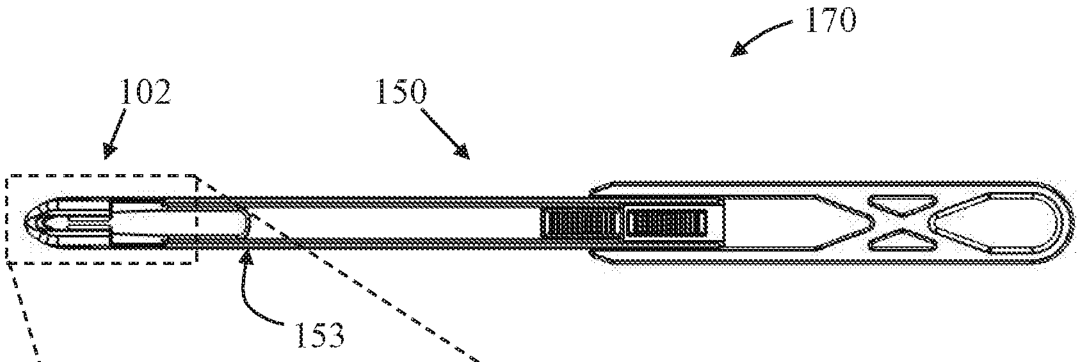
FIGS. 11A-11H illustrate views showing components of the exemplary kit shown in FIG. 10 representing scenarios in an exemplary sequence of deploying a vascular access port, in accordance with some embodiments.
Figure 11B:
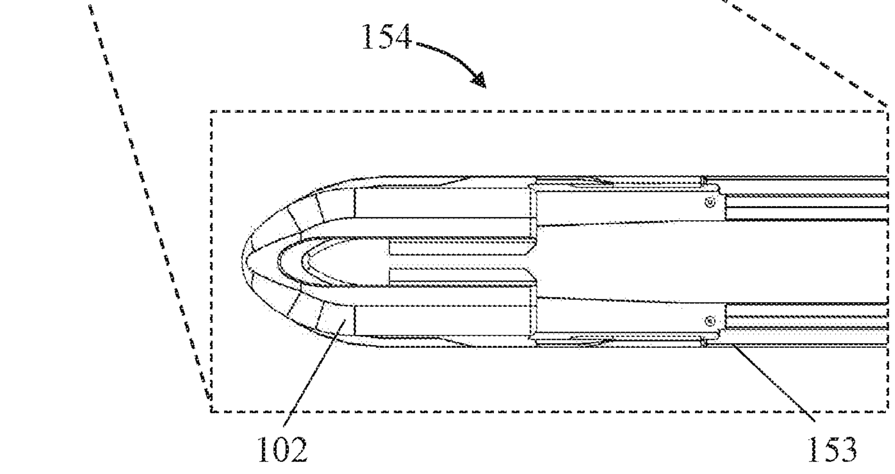

FIG. 10 illustrates an exemplary kit 170 which includes port body 101 and port body extension 102 of implant (vascular access port) 100, port delivery apparatus 150, and optionally also a catheter 180 (which may be at least similar in intended use, in function and/or in structure, to catheter 15 shown in FIGS. 1A and 1B). Optionally and alternatively, kit 170 excludes port body 101 and/or catheter 180, which may be provided separately. FIGS. 11A-11H schematically illustrate views represent optional scenarios in an exemplary sequence of deploying implant 100 using port delivery apparatus 150. FIG. 11A is a top view showing an exemplary preliminary scenario, optionally following unpackaging of kit 170 and before implantation of implant 100. FIG. 11B is a zoom-in view of a portion of FIG. 11A showing distal portion 154 with port body extension 102 in greater detail. As shown, port delivery apparatus 150 is releasably connected to port body extension 102, which is held fixedly with prongs 161 projecting upwardly to a maximal extend through openings 162 of distal portion 154 of support member 153.

Figure 11C:
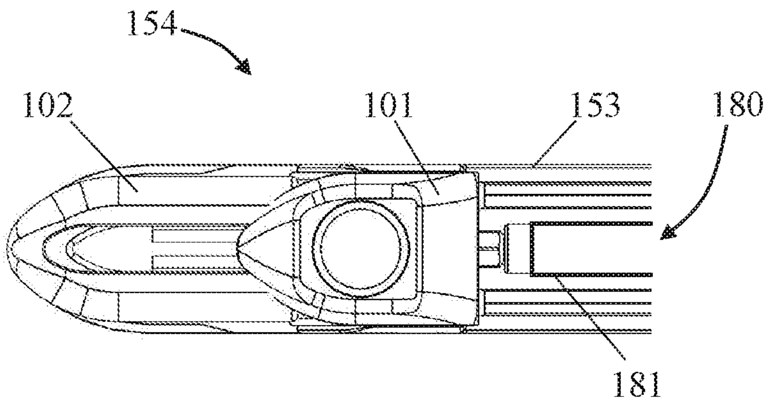
Figure 11D:
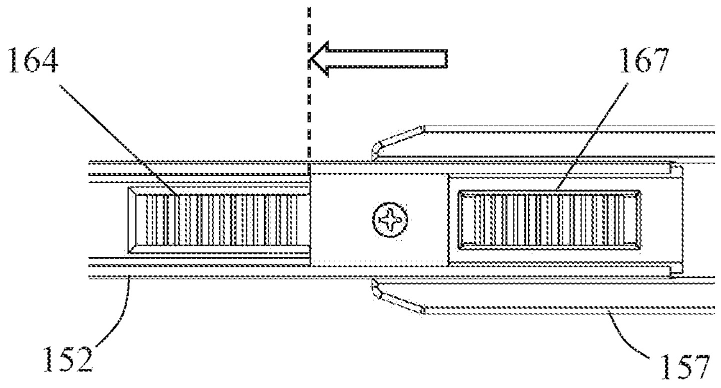

FIG. 11C shows same portion of port delivery apparatus 150 as in FIG. 11B after coupling port body 101 thereto. Coupling may include interengaging proximal or distal ends of lateral barriers 158 of support member 153 with distal or proximal ends, respectively, of the corresponding grooves 106 extending longitudinally on the sides of port body inferior portion 116, and sliding port body 101 forward (distally) or backward along sliding surface 155 until reaching its docking location 167, such that vascular access port 100 is in the delivery configuration (shown in FIG. 11C). Port body 101 may be held in docking location 167 using bumps 168 (shown in FIG. 9D), optionally configured for increasing local friction on sliding surface 155, although other holding means can be applied.

When in the delivery configuration, port body 101 and port body extension 102 are disconnected and at least partially separated from each other, and port delivery apparatus 150 is configured to maintain a fixed gap, formed between respective boundaries of port body 101 and port body extension 102, the gap being optionally at least about 5 mm, optionally at least 10 mm, optionally at least 20 mm, in length. As shown, in the delivery configuration, port body extension 102 is contracted such that sides thereof are not protruding laterally from boundaries of port delivery apparatus 150. As such, distal portion 154 fixated with port body extension 102 is configured to function as a front portion of a surgical tunneling apparatus (or "tunneler").

In some embodiments, port delivery apparatus 150 and/or support member 153, or distal portion 154 thereof, has maximal width (between lateral boundaries thereof) of about 25 mm or less, optionally about 20 mm or less, or optionally about 15 mm or less; In some such embodiments, the width of port body 101 and/or the laterally collapsed port body extension 102, when in the delivery configuration, is optionally about the size of the maximal width of port delivery apparatus 150 and/or support member 153, or distal portion 154 thereof, or at least about 1 mm, optionally at least about 2 mm, smaller therefrom. When in the deployment configuration, in which port body extension 102 is fully assembled with port body 101, vascular access port 100 as a unified structure has a width greater than greater than the maximal width of port delivery apparatus 150 and/or support member 153, or distal portion 154 thereof, such as by at least 1 mm, optionally by at least 5 mm, or optionally by at least 10 mm. In an exemplary embodiment, the maximal width of port delivery apparatus 150 and/or support member 153, or distal portion 154 thereof, is about 15 mm; the width of port body 101 and/or the laterally collapsed port body extension 102, when in the delivery configuration, is about 13 mm; and the width of vascular access port 100 in the deployed configuration is about 22 mm.

Via an incision in a body of the subject, a subcutaneous void is formed between or beneath skin tissue layers at a target implantation site in the subject body, similarly to as shown in FIG. 1A, and as explained in the related description. If the target implantation site is substantially remote from the incision (e.g., distance therebetween is a few centimeters long, optionally greater than about 5 cm), then a subcutaneous surgical tunnel is first created between the incision and the target implantation site, and the subcutaneous void can be formed via the surgical tunnel or considered as the distal portion of the surgical tunnel, similarly to as shown in FIGS. 5B and 50, and as explained in the related description. The incision and optionally also part of the surgical tunnel and/or void can be formed with any applicable surgical instrument(s). Optionally, the subcutaneous surgical tunnel and/or void is created at least in part using distal end 154 (with port body extension 102 connected thereto), such as by pushing and/or manipulating port delivery apparatus 150 via its proximal end (e.g., via handle 157). Optionally, alternatively or additionally, the subcutaneous surgical tunnel and/or void is initially created or cut using dissection tip 156 which projects distally relative to distal boundaries of port body extension 102.

Catheter 180 may be provided as part of kit 170 or separately. In some embodiments, a proximal end 181 of catheter 180 is already connected to port body 101 via connector 117, for example immediately before unpackaging of kit 170. Optionally and alternatively, prior to implantation, the proximal end of catheter 180 is connected to connector 117 cavity such that cavity 115 of the vascular access port is in fluid communication with lumen 182 (shown in FIG. 11F) of catheter 180. A distal end of catheter 180, opened to catheter lumen 182, is positioned in vasculature of the subject, optionally including along a length of a superior vena cava, similarly to as shown in FIGS. 1A and 1B, and as explained in the related description. Port delivery apparatus 150, equipped with the disassembled vascular access port 100 in the delivery configuration, is then pushed through the surgical tunnel to the subcutaneous void, optionally in the course of creating the surgical tunnel and/or void as described. This results in inserting at least distal portion 154 with port body extension 102 into the subcutaneous void.

Figure 11E:
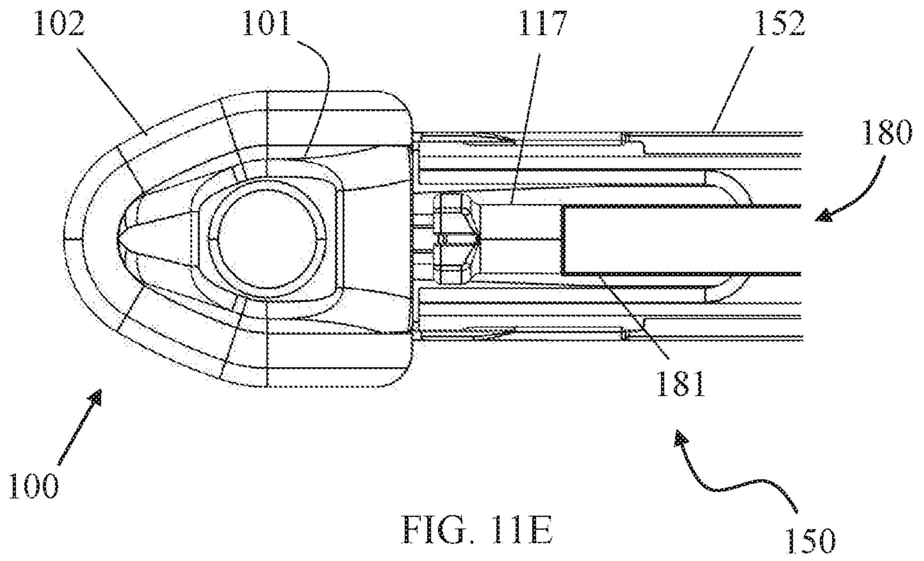
Figure 11F:
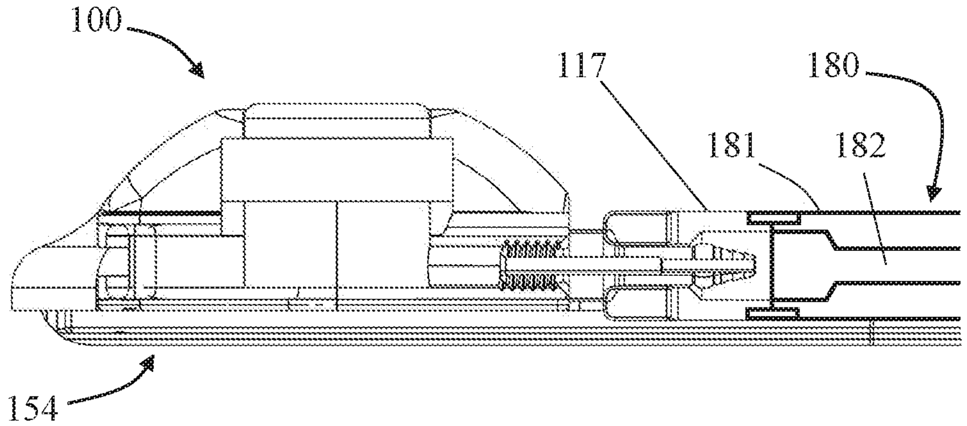

Once in proper position, as may be verified using imaging or palpation, vascular access port 100 can be deployed, using port delivery apparatus 150. Deploying vascular access port 100 is accomplished by pushing port body 101 with first actuator 164 (FIG. 11D) to slide distally on sliding surface 155, thereby diminishing the gap therebetween until engaging port body 101 with port body extension 102 and forcing them to adjoin and fixedly connect with each other (FIGS. 11E and 11F). As such, vascular access port 100 is changed (transfers or transformed) into the deployed configuration such that its unified structure is greater in volume than port body 101 optionally by at least 15%, or by at least 30%. Increase in volume of implant (vascular access port) 100 optionally also forces an increase in total volume enclosed by the subcutaneous void. This can be accomplished by way of forcing port body extension 102 to expand laterally, by pushing the external surface of port body 102 against internal surface 107 of port body extension 102, similarly to as shown in FIGS. 5C, 7D and 7E, and as explained in the related description. The laterally shifted edges of port body extension 102 can cause stretching, separating and/or dissecting tissue layers forming the subcutaneous void thus increasing subcutaneous void volume and/or stabilizing and/or fixating port body 101 in the subcutaneous void. Increasing the volume of the subcutaneous void can also result in compaction of tissue mass surrounding port body extension 102, thereby increasing fixation and/or stability of vascular access port body 100 in the target implantation site.

Figure 11G:
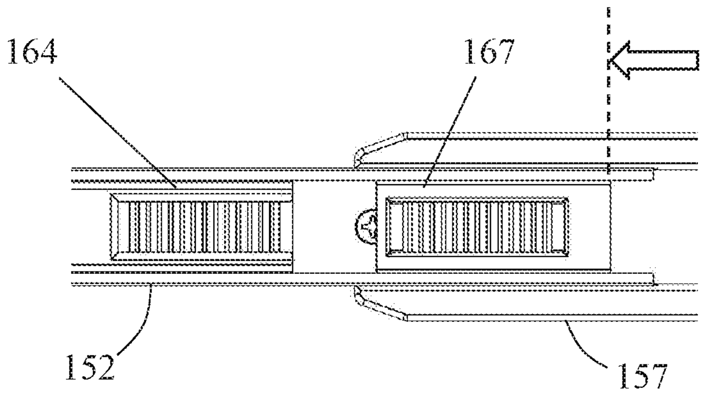
Figure 11H:
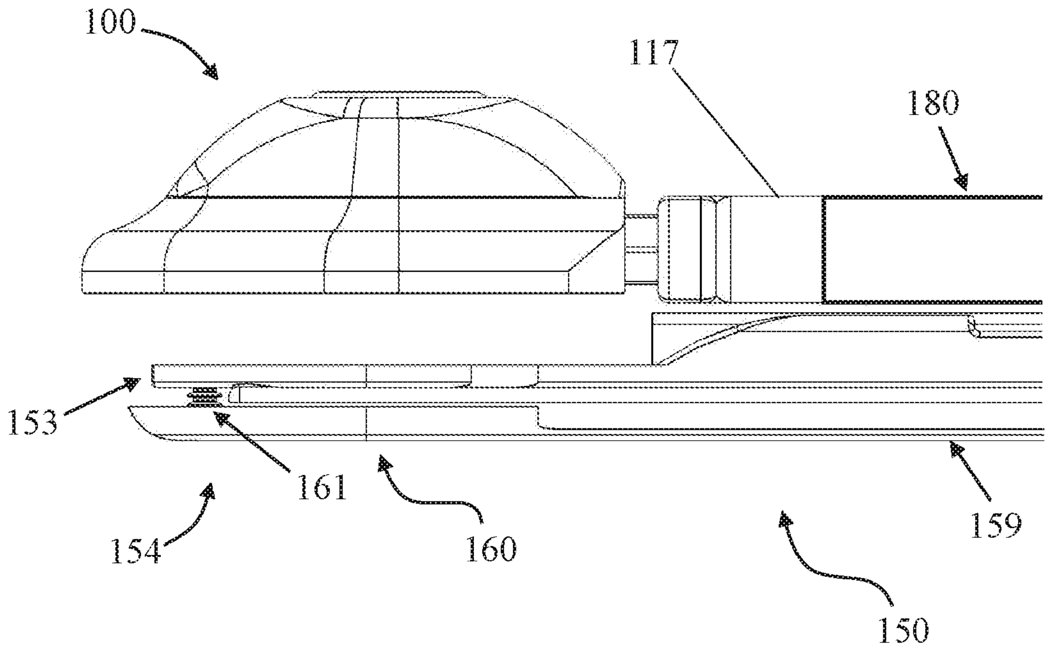

Once changed into deployed configuration, as may be verified using imaging or palpation, vascular access port 100 can be released from port delivery apparatus 150. This is accomplished by shifting releasing element 165 distally using second actuator 167 (as shown in FIG. 11G) until distal portion 166 of releasing element 165 detach and space distal portion 160 of base member 159 from distal portion of support member 153. This causes retraction of prongs 161 from port body extension 102 and therefore from the unified structure forming vascular access port 100, as shown in FIG. 11H. After release, port delivery apparatus 150 can be removed from the surgical tunnel. Following extraction of port delivery apparatus 150 the insertion incision can be sutured or bonded using adhesive.

Each of the following terms written in singular grammatical form: ‘a’, ‘an’, and ‘the’, as used herein, means ‘at least one’, or ‘one or more’. Use of the phrase ‘one or more’ herein does not alter this intended meaning of ‘a’, ‘an’, or ‘the’. Accordingly, the terms ‘a’, ‘an’, and ‘the’, as used herein, may also refer to, and encompass, a plurality of the stated entity or object, unless otherwise specifically defined or stated herein, or, unless the context clearly dictates otherwise. For example, the phrases: ‘a unit’, ‘a device’, ‘an assembly’, ‘a mechanism’, ‘a component’, ‘an element’, and ‘a step or procedure’, as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: ‘includes’, ‘including’, ‘has’, ‘having’, ‘comprises’, and ‘comprising’, and, their linguistic/grammatical variants, derivatives, or/and conjugates, as used herein, means ‘including, but not limited to’, and is to be taken as specifying the stated component(s), feature(s), characteristic(s), parameter(s), integer(s), or step (s), and does not preclude addition of one or more additional component(s), feature(s), characteristic(s), parameter(s), integer(s), step(s), or groups thereof. Each of these terms is considered equivalent in meaning to the phrase ‘consisting essentially of’.

The term ‘method’, as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range ‘from 1 to 6’ also refers to, and encompasses, all possible sub-ranges, such as ‘from 1 to 3’, ‘from 1 to 4’, ‘from 1 to 5’, ‘from 2 to 4’, ‘from 2 to 6’, ‘from 3 to 6’, etc., and individual numerical values, such as ‘1’, ‘1.3’, ‘2’, ‘2.8’, ‘3’, ‘3.5’, ‘4’, ‘4.6’, ‘5’, ‘5.2’, and ‘6’, within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C', and is considered equivalent to, and meaning the same as, the phrase 'room temperature refers to a temperature in a range of from about 20° C. to about 25° C'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. A vascular access port, comprising:

a port body having a longitudinal axis, coupled with a septum member covering a cavity defined by the port body; and a deformable port body extension configured to form with the port body a unified structure having final shape and size;

the vascular access port is changeable subcutaneously to a deployed configuration by decreasing in length parallel to the longitudinal axis and/or expanding transversely to the longitudinal axis, wherein the port body extension envelopes a front end and two opposing sides of the port body.

2. The vascular access port of claim 1, wherein the unified structure is greater in volume than the port body by at least 15%, and/or has a lower surface area to volume ratio than the combined port body and port body extension when in a delivery configuration, and/or has a base surface area greater than a base surface area of the port body by at least 30%.

3. The vascular access port of claim 1, wherein the port body is configured to interlock with the port body extension when the vascular access port is in the deployed configuration.

4. The vascular access port of claim 1, wherein the port body extension includes a front edge pointing distally away from the port body and configured to cause atraumatic separation of tissue layers when forced to pass therebetween.

5. The vascular access port of claim 1, wherein the port body is configured to deform the port body extension, when the vascular access port changes to the deployed configuration.

6. The vascular access port of claim 1, wherein the port body extension is configured to deform when a portion of the port body is pushed against an inner surface of the port body extension.

7. The vascular access port of claim 1, wherein the port body extension has lateral edges configured to stretch, separate and/or dissect tissue layers when forced to pass therebetween, when the vascular access port changes to the deployed configuration.

8. The vascular access port of claim 1, wherein the port body is configured to maintain size and shape thereof when the vascular access port changes to the deployed configuration.

9. The vascular access port of claim 1, wherein the port body extension is configured to stabilize and/or fixate the port body in-place in a target implantation site in the subject body when the vascular access port changes to the deployed configuration.

10. The vascular access port of claim 1, wherein the port body has an inferior portion and a posterior portion, the inferior portion surrounds the cavity and the posterior portion is connected to the septum member, wherein the port body extension envelopes the front end and two opposing sides of the port body inferior portion when the vascular access port is in the deployed configuration.

11. The vascular access port of claim 1, configured to increase in cross-sectional area when changing to the deployed configuration.

12. A method for deploying a vascular access port in a body of a subject, the method comprising:

forming a subcutaneous void between or beneath skin tissue layers at a target implantation site in the subject body;

inserting the vascular access port into the subcutaneous void, wherein the vascular access port includes a port body and a deformable port body extension configured to form with the port body a unified structure having final shape and size; and deploying the vascular access port, wherein the vascular access port changes to a deployed configuration by decreasing in length parallel to the longitudinal axis and/or expanding transversely to the longitudinal axis, wherein the port body extension envelopes a front end and two opposing sides of the port body.

13. The method of claim 12, wherein the port body is coupled with a septum member covering a cavity defined by the port body.

14. The method of claim 12, wherein the deploying forces an increase in total volume enclosed by the subcutaneous void.

15. The method of claim 12, wherein the deploying includes forcing the port body extension to expand laterally by pushing a portion of the port body against an internal surface of the port body extension.

16. The method of claim 15, wherein the port body extension has lateral edges configured to shift laterally when the port body extension expands laterally, wherein the deploying includes stretching, separating or dissecting tissue layers forming the subcutaneous void with the lateral edges of the port body extension.

17. The method of claim 12, further comprising:

creating a subcutaneous surgical tunnel between a first incision and the target implantation site; and delivering the vascular access port through the surgical tunnel to the subcutaneous void.

18. A kit for implanting a vascular access port in a host, the kit comprising:

a vascular access port according to claim 1; and a port delivery apparatus releasably connectable to the port body of the vascular access port according to claim 1 and to the port body extension of the vascular access port according to claim 1 and configured for selectively changing the vascular access port according to claim 1 to the deployed configuration.

19. A kit according to claim 18, wherein the port delivery apparatus includes a dissection tip configured for projecting distally relative to distal boundaries of the port body extension when attached to the delivery apparatus body.

20. A kit according to claim 18, further comprising a catheter connected or connectable to the port body for facilitating fluid communication between the cavity and a lumen enclosed by the catheter.

* * * * *